(12) United States Patent
Weber et al.

(10) Patent No.: US 6,221,150 B1
(45) Date of Patent: Apr. 24, 2001

(54) PERYLENE COMPOUNDS AND PIGMENT PREPARATIONS

(75) Inventors: Joachim Weber, Frankfurt; Manfred Urban, Wiesbaden; Erwin Dietz, Koenigstein, all of (DE)

(73) Assignee: Clariant GmbH, Frankfurt (DE)

( * ) Notice: Subject to any disclaimer, the term of this patent is extended or adjusted under 35 U.S.C. 154(b) by 0 days.

(21) Appl. No.: 09/255,252

(22) Filed: Feb. 22, 1999

(30) Foreign Application Priority Data

Feb. 21, 1998 (DE) .............................................. 198 07 422
Aug. 6, 1998 (DE) .............................................. 198 35 757

(51) Int. Cl.$^7$ .......................... C07D 471/06; C09B 5/62; C09B 67/22
(52) U.S. Cl. .......................... 106/498; 106/493; 106/494; 106/495; 106/496; 106/497; 106/413; 546/37
(58) Field of Search .................... 106/498, 493, 106/494, 495, 496, 497, 413; 546/37

(56) References Cited

U.S. PATENT DOCUMENTS

| | | | |
|---|---|---|---|
| 4,310,359 | 1/1982 | Ehashi et al. | 106/288 Q |
| 4,762,569 | 8/1988 | Miki et al. | 106/476 |
| 4,986,852 | 1/1991 | Dietz et al. | 106/498 |
| 5,110,931 | * 5/1992 | Dietz et al. | 546/37 |
| 5,264,034 | * 11/1993 | Dietz et al. | 106/498 |
| 5,466,807 | 11/1995 | Dietz et al. | 546/6 |
| 5,753,030 | * 5/1998 | Flatt et al. | 106/495 |
| 5,808,073 | * 9/1998 | Bohm et al. | 546/39 |
| 5,958,129 | * 9/1999 | Urban et al. | 106/498 |

FOREIGN PATENT DOCUMENTS

| | | |
|---|---|---|
| 3106906 | 1/1982 | (DE) . |
| 3436206 | * 4/1986 | (DE) . |
| 3926563 | 2/1991 | (DE) . |
| 299733 | 5/1992 | (DE) . |
| 0046164 | 2/1982 | (EP) . |
| 0302973 | 2/1989 | (EP) . |
| 0321919 | 6/1989 | (EP) . |
| 0864613 | 9/1998 | (EP) . |
| 5-117541 | 5/1993 | (JP) . |

OTHER PUBLICATIONS

European Search Report (Jun. 1999).
XP–002106704 "Molecular Structure and Photoactivity in Perylene Tetracaroxylic Diimides," J. Duff, A. Hor, R. Loutfy, and A. Melnyk, Chem. Funct. Dyes, Proc. Int. Symp., 2$^{nd}$ 1992, 1993, pp. 564–571.

Derwent Patent Family Report and/or Abstracts (Jun. 1999).
XP 002106705, AN 93–191685, Abstract of JP 5–117541 (May 1993).

* cited by examiner

Primary Examiner—Anthony Green
(74) Attorney, Agent, or Firm—Susan S. Jackson; Scott E. Hanf

(57) ABSTRACT

The present invention relates to pigment dispersants of the formula (I)

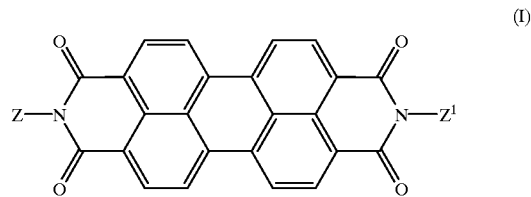

(I)

in which
$Z^1$ is a radical of the formula (Ia)

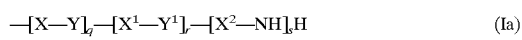

(Ia)

in which
X, $X^1$ and $X^2$ are identical or different and are a branched or unbranched $C_2$–$C_6$-alkylene radical or a $C_5$–$C_7$-cycloalkylene radical which can be substituted by from 1 to 4 $C_1$–$C_4$-alkyl radicals, hydroxyl radicals, and/or by from 1 to 2 further $C_5$–$C_7$-cycloalkyl radicals;

Y and $Y^1$ are identical or different and are an NH—, —O— or N($C_1$–$C_6$-alkyl) group, q is a number from 1 to 6, r and s independently of one another are a number from 0 to 6, but are not simultaneously zero; and Z is defined as $Z^1$, $Z^2$ or $Z^3$, where $Z^2$ is a radical of the formula (Ib)

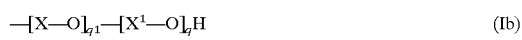

(Ib)

in which
q1 is a number from 0 to 6, and $Z^3$ is hydrogen, hydroxyl, amino or $C_1$–$C_6$-alkyl where the alkyl group can be substituted by from 1 to 4 substituents from the group consisting of Cl, Br, CN, OH, $C_6H_5$, carbamoyl, $C_1$–$C_4$-acyl, $C_1$–$C_4$-alkoxy and $NR^2R^3$, and to pigment preparations comprising organic base pigments and pigment dispersants, and to prepared pigment formulations prepared from the pigment preparations.

17 Claims, No Drawings

PERYLENE COMPOUNDS AND PIGMENT PREPARATIONS

CROSS-REFERENCES TO RELATED APPLICATIONS

The present invention is described in the German priority applications Nos. 198 07 422.0, filed Feb. 21, 1998 and 198 35 757.5, filed Aug. 6, 1998, which are hereby incorporated by reference as is fully disclosed herein.

BACKGROUND OF THE INVENTION

Pigment preparations are combinations of pigments with pigment dispersants that are structurally analogous to pigments and are substituted by groups having a specific activity. They are added to the pigments in order to facilitate dispersion in the application media, especially in varnishes, and to improve the rheological and coloristic properties of the pigments. The viscosity of the highly pigmented paint concentrates (millbase) is lowered and the flocculation of the pigment particles is lessened. By this means it is possible, for example, to increase the transparency, which is desirable especially in the case of metallic pigments.

A large number of proposals exist for improving the rheological and coloristic properties of organic pigments by adding pigment dispersants, although not always with the desired result.

EP-B-0 321 919 describes the preparation of pigment preparations by mixing the base pigments with pigment derivatives that contain methyleneimidazolyl groups. In the field of perylene pigments, this results in pigment preparations whose coloristic properties no longer meet current requirements.

DE-A-3 106 906 describes the preparation of pigment dispersants that contain sulfonamide groups. The pigment dispersants described therein are based on perylene compounds but have considerable coloristic and rheological deficiencies.

U.S. Pat. No. 4,762,569 describes the preparation of pigment preparations on the basis of symmetrical perylene-3,4,9,10-tetracarboxylic diimides. These pigment preparations are suitable only for use in solventborne systems. They do not meet all of the requirements in terms of rheological and coloristic properties that are made of pigment preparations. At high pigment dispersant contents in particular the coloristic properties are no longer adequate and in many cases a distinct loss of gloss and marked shade deviation can be noted. Furthermore, these pigment dispersants possess inadequate solvent fastness and fastness to overcoating, thus greatly restricting their universal application. Moreover, in many varnish systems it is possible to observe instances of incompatibility with the binder, which is prohibitive for their use.

SUMMARY OF THE INVENTION

The present invention relates to novel pigment dispersants and pigment preparations having improved coloristic and rheological properties and to their preparation and use for pigmenting high molecular mass materials. The object was therefore to provide pigment preparations which overcome the abovementioned disadvantages of the prior art in terms of coloristics, rheology and universal applicability.

It has been found that the object is surprisingly achieved by pigment preparations which in addition to the base pigments comprise one or more particular perylene-3,4,9,10-tetracarboxylic diimides.

DESCRIPTION OF THE PREFERRED EMBODIMENTS

The invention provides perylene compounds of the formula (I)

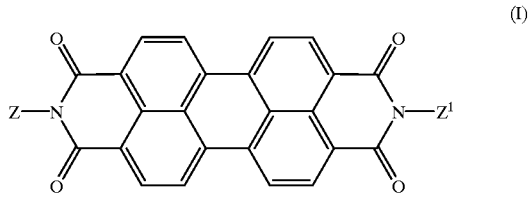

in which
Z$^1$ is a radical of the formula (Ia)

$$-[X-Y]_q-[X^1-Y^1]_r-[X^2-NH]_sH \qquad (Ia)$$

in which

X, X$^1$ and X$^2$ are identical or different and are a branched or unbranched C$_2$–C$_6$-alkylene radical or a C$_5$–C$_7$-cycloalkylene radical which can be substituted by from 1 to 4 C$_1$–C$_4$-alkyl radicals, hydroxyl radicals, hydroxyalkyl radicals having 1 to 4 carbon atoms, and/or by from 1 to 2 further C$_5$–C$_7$-cycloalkyl radicals;

Y and Y$^1$ are identical or different and are an NH—, —O— or N(C$_1$–C$_6$-alkyl) group, preferably —NCH$_3$ or

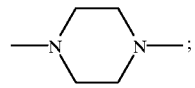

q is a number from 1 to 6, preferably 1, 2, 3 or 4;

r and s independently of one another are a number from 0 to 6, preferably 0, 1 or 2, but are not simultaneously zero, and s is different from zero, if Y$^1$ is —O—; and Z is defined as Z$^1$, Z$^2$ or Z$^3$, where Z$^2$ is a radical of the formula (Ib)

$$-[X-O]_{q1}-[X^1-O]_qH \qquad (Ib)$$

in which q1 is a number from 0 to 6, preferably 0, 1, 2, 3 or 4;

and Z$^3$ is hydrogen, hydroxyl, amino or C$_1$–C$_8$-alkyl where the alkyl group can be substituted by from 1 to 4 substituents from the group consisting of Cl, Br, CN, OH, C$_6$H$_5$, carbamoyl, C$_1$–C$_4$-acyl, C$_1$–C$_4$-alkoxy and NR$^2$R$^3$, or is perfluorinated or partly fluorinated, and where R$^2$ and R$^3$ independently of one another are a hydrogen atom, a substituted or unsubstituted or partly fluorinated or perfluorinated alkyl group of 1 to 20 carbon atoms, or a substituted or unsubstituted or partly fluorinated or perfluorinated alkenyl group of 2 to 20 carbon atoms, where the substituents can be hydroxyl, phenyl, cyano, chloro, bromo, C$_2$–C$_4$-acyl or C$_1$–C$_4$-alkoxy, or R$^2$ and R$^3$, together with the nitrogen atom, form a saturated, unsaturated or aromatic heterocyclic ring which if desired contains a further nitrogen, oxygen or sulfur atom in the ring.

Depending on the selection of the radicals Z and Z$^1$ symmetrical or asymmetrical pigment dispersants of the formula (I) are obtained. Asymmetrical pigment dispersants of the formula (I) include those having different radicals $Z^1$.

Preference is given to perylene compounds of the formula (I) in which X, $X^1$ and $X^2$ are a $C_2$–$C_4$-alkylene radical or cyclohexylene.

Of particular interest, for example, are perylene compounds of the formula (I) in which $Z^1$ has one of the definitions —$(CH_2)_3$—NH—$(CH_2)_3$—$NH_2$, —$(CH_2)_2$—NH—$(CH_2)_2$—$NH_2$, —$(CH_2)_3$—NH—$(CH_2)_2$—NH—$(CH_2)_3$—$NH_2$,

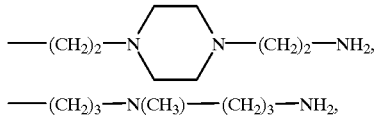

—$(CH_2)_3$—N$(CH_3)$—$(CH_2)_3$—$NH_2$,

—$(CH_2)_3$—O—$(CH_2)_2$—O—$(CH_2)_3$—$NH_2$, —$(CH_2)_3$—O—$(CH_2)_3$—O—$(CH_2)_3$—$NH_2$,
—$(CH_2)_2$—NH—$(CH_2)_3$—$NH_2$,
—$(CH_2)_3$—NH—$(CH_2)_3$—$NH_2$,
—$(CH_2)_3$—NH—$(CH_2)_2$—$NH_2$,
—$(CH_2)_2$—NH—$(CH_2)_2$—NH—$(CH_2)_2$—$NH_2$,
—$(CH_2$—$CH_2$—NH$)_4$—H, —$(CH_2$—$CH_2$—NH$)_5$—H or
—$(CH_2)_3$—O—$(CH_2)_4$—O—$(CH_2)_3$—$NH_2$.

Examples of perylene compounds of interest are those of the formula (I) in which $Z^2$ has one of the definitions —$CH(CH_2OH)_2$ or —$(CH_2)_2$—O—$(CH_2)_2OH$.

Also of interest, for example, are perylene compounds of the formula (I) in which $Z^3$ is hydrogen, benzyl, $C_1$–$C_6$-alkyl or a $C_2$–$C_6$-alkyl which is substituted by from 1 to 2 substituents from the group consisting of hydroxyl, acetyl, methoxy and ethoxy, and with particular preference is hydrogen, methyl, ethyl, propyl, butyl, benzyl, hydroxyethyl, hydroxypropyl or methoxypropyl.

Of further interest are perylene compounds of the formula (I) in which $Z^3$ is a radical of the group —$(CH_2)_n$—$NR^2R^3$ in which n is a number from 1 to 6, preferably from 2 to 4, and $R^2$ and $R^3$ independently of one another are a hydrogen atom, a $C_1$–$C_6$-alkyl group, a $C_1$–$C_6$-alkyl group which is substituted by from 1 to 2 substituents from the group consisting of hydroxyl, acetyl, methoxy, ethoxy, chloro and bromo, or $R^2$ and $R^3$, together with the adjacent nitrogen atom, form an imidazolyl, piperidinyl, morpholinyl, pipecolinyl, pyrrolyl, pyrrolidinyl, pyrazolyl or piperazinyl ring.

Of particular interest in this context are perylene compounds in which n is the number 2 or 3, and $R^2$ and $R^3$ are each a methyl or ethyl group or $R^2$ and $R^3$, together with the adjacent nitrogen atom, form an imidazolyl, piperazinyl or morpholinyl radical.

The present invention also provides a process for preparing the perylene compounds of the formula (I) by reacting perylene-3,4,9,10-tetracarboxylic monoanhydride monoimides of the formula (IIa)

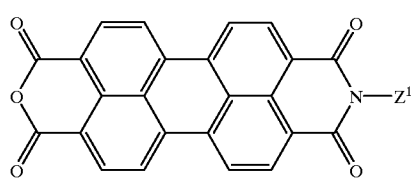

(IIa)

with one or more, preferably 1 or 2, amines of the formula (IIIa) or (IIIb)

Z—$NH_2$ (IIIa)

$Z^1$—$NH_2$ (IIIb);

or by reacting perylene-3,4,9,10-tetracarboxylic monoanhydride monoimides of the formula (IIb)

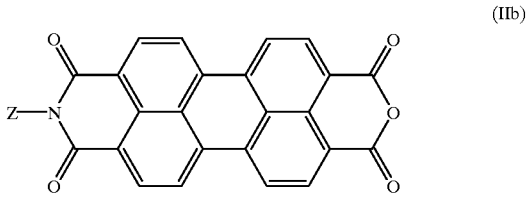

(IIb)

with one or more, preferably 1 or 2, amines of the formula (IIIb); or by reacting perylene-3,4,9,10-tetracarboxylic dianhydride of the formula (IIc)

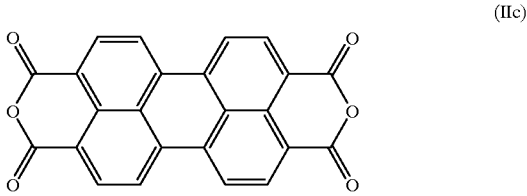

(IIc)

with one or more, preferably 1 or 2, amines of the formula (IIIb).

The anhydride groups in the formulae (IIa), (IIb) and (IIc) can also be present as dicarboxylic acids.

The reaction according to the invention can be conducted in an aqueous, organic or aqueous-organic medium at temperatures from 0 to 200° C., preferably from 20 to 180° C. Suitable as the organic medium are inert organic solvents, preferably those whose boiling point is above that of water, examples being DMSO, chlorobenzene, dichlorobenzenes, trichlorobenzenes, relatively high-boiling alcohols, carboxamides, and relatively high-boiling ethers. In addition, the amines of the formula (IIa) or (IIIb) may serve simultaneously as solvents. The pH of the aqueous or aqueous-organic medium can be acidic, neutral or alkaline and is preferably from 3 to 14. It is also possible to employ different amines simultaneously in order to prepare mixtures of perylene compounds of the formula (I).

With particular preference, the condensation is conducted in aqueous solution under alkaline pH conditions at temperatures in the range between 50 and 180° C. In this case it is judicious to employ the amines in excess, judiciously in an up to 8-fold, preferably an up to 4-fold, molar excess. The resultant process products of the formula (I) are preferably isolated from the reaction mixture by filtration.

Examples of amines of the formula (IIIa) which can be employed are ammonia, methylamine, ethylamine, propylamine, butylamine, β-hydroxyethylamine, N,N-dimethylaminopropylenediamine, N,N-diethylaminopropylenediamine, N,N-dimethylaminoethylenediamine, N-methylaminopropylenediamine, β- or γ-hydroxypropylamine, 2-(2-aminoethoxy)ethanol, hydroxylamine or hydrazine.

Examples of amines of the formula (IIIb) which can be employed are diethylenetriamine, triethylenetetramine, tetraethylenepentamine, pentaethylenehexamine, dipropylenetriamine, N,N-bis(3-aminopropyl)methylamine, tripropylenetetramine, 3-(2-aminoethyl)- aminopropylamine, N,N'-bis(3-aminopropyl) ethylenediamine, 4,7dioxadecane-1,10-diamine, 4,9-dioxadodecane-1,12-diamine or 1,4-bis-(3-aminopropoxy) butane.

The perylene compounds of the formula (I) of the invention are used, for example, to prepare pigment preparations.

The present invention also provides pigment preparations comprising
a) at least one organic base pigment and
b) at least one pigment dispersant of the formula (IV)

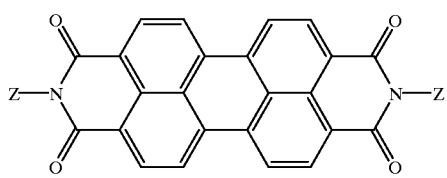

(IV)

in which the two radicals Z are identical or different and are as defined above with the proviso that the two radicals Z are not simultaneously $Z^3$.

The pigment dispersants of the formula (IV) can be prepared by processes analogous to those for preparing the perylene compounds of the formula (I).

By base pigments are meant organic pigments or mixtures of organic pigments, which may also be present in the form of customary pigment preparations.

Examples of suitable base pigments for the preparation of the pigment preparations of the invention are perylene, perinone, phthalocyanine, dioxazine, quinacridone, azo, anthraquinone, aminoanthraquinone, thioindigo, diketopyrrolopyrrole, flavanthrone, indanthrone, isoindoline, isoindolinone, anthrapyrimidine, pyranthrone, quinophthalone, isoviolanthrone, triarylcarbonium, carbon black and anthanthrone pigments, or mixtures thereof. It is also possible to employ more than one base pigment.

Examples of preferred base pigments for the purposes of the present invention are C.I. Pigment Red 123 (C.I. No. 71145), C.I. Pigment Red 149 (C.I. No. 71137), C.I. Pigment Red 178 (C.I. No. 71 155), C.I. Pigment Red 179 (C.I. No. 71 130), C.I. Pigment Red 190 (C.I. 71 140), C.I. Pigment Red 224 (C.I. No. 71 127), C.I. Pigment Violet 29 (C.I. No. 71 129); C.I. Pigment Orange 43 (C.I. No. 71 105), C.I. Pigment Red 194 (C.I. No. 71 100); C.I. Pigment Violet 19 (C.I. No. 73 900), C.I. Pigment Red 122 (C.I. No. 73 915); C.I. Pigment Red 209 (C.I. No. 73 905); C.I. Pigment Yellow 147, C.I. Pigment Red 168 (C.I. No. 59 300); C.I. Pigment Yellow 120 (C.I. No. 11 783); C.I. Pigment Yellow 151 (C.I. No. 13 980), C.I. Pigment Brown 25 (C.I. No. 12 510), C.I. Pigment Violet 32 (C.I. No. 12 517), C.I. Pigment Red 170 (C.I. No. 12 475), C.I. Pigment Orange 38 (C.I. No. 12 367), C.I. Pigment Red 188 (C.I. No. 12 467), C.I. Pigment Red 187 (C.I. No. 12 486), C.I. Pigment Orange 34 (C.I. No. 21 115), C.I. Pigment Orange 13 (C.I. No. 21 110), C.I. Pigment Red 9 (C.I. No. 12 460), C.I. Pigment Red 2 (C.I. No. 12 310), C.I. Pigment Red 112 (C.I. No.12 340), C.I. Pigment Red 7 (C.I. No. 12 420), C.I. Pigment Red 210 (C.I. No.12 477), C.I. Pigment Red 12 (C.I. No.12 385), C.I. Pigment Red 202 (C.I. No. 73 907), C.I. Pigment Blue 60 (C.I. No. 69 800), C.I. Pigment Green 7 (C.I. No. 74 260), C.I. Pigment Green 36 (C.I. No. 74 265), C.I. Pigment Blue 15:1,15:2, 15:3,15:4 and 15 (C.I. No. 74 160), C.I. Pigment Blue 56 (C.I. No. 42 800), C.I. Pigment Blue 61 (C.I. No.42 765:1), C.I. Pigment Violet 37 (C.I. No. 51 345), C.I. Pigment Red 177 (C.I. No. 65 300), C.I. Pigment Red 254 (C.I. No. 56 110), C.I. Pigment Red 255, 264, C.I. Pigment Orange 73, C.I. Pigment Violet 23 (C.I. No. 51 319) and C.I. Pigment Red 88 (C.I. No. 73312).

The amount of the pigment dispersants of the formula (IV) in the pigment preparations of the invention can vary within wide limits provided it does not impact adversely on the target pigment quality; generally, however, the preparations include a content of from 0.5 to 40% by weight, in particular from 1 to 20% by weight, of at least one of the pigment dispersants of the formula (IV), based on the weight of the base pigment.

In addition to the base pigment and the pigment dispersants of the formula (IV) the pigment preparations of the invention may also include further customary additives, such as fillers, standardizing agents, surface-active agents, resins, defoamers, antidust agents, extenders, colorants, preservatives, and drying retardants. Said colorants are employed preferably for shading.

Of further interest are pigment preparations comprising
a) at least one organic base pigment,
b1) a pigment dispersant of the formula (IX)

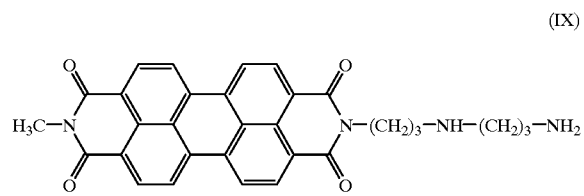

(IX)

and
b2) a pigment dispersant of the formula (X)

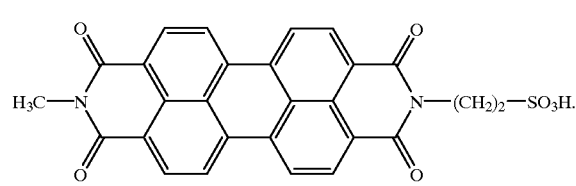

(X)

The proportions of the pigment dispersant b1) to b2) can be between 1:10 and 10:1 parts by weight, preferably between 1:5 and 5:1 parts by weight, in particular between 1:3 and 3:1 parts by weight.

Preferred pigment preparations in the context of the present invention consist essentially of
a) from 40 to 99.5% by weight, preferably from 60 to 99% by weight, of at least one base pigment,
b) from 0.5 to 40% by weight, preferably from 1 to 20% by weight, of at least one, preferably 1, 2 or 3, pigment dispersants of the formula (IV),
c) from 0 to 20% by weight, preferably from 0.1 to 15% by weight, of surface-active agents, and
d) from 0 to 20% by weight, preferably from 0.1 to 10% by weight, of other customary additives,
the proportions of the respective components being based on the overall weight of the preparation (100% by weight).

Suitable surface-active agents are customary anionic, cationic and nonionic surfactants, examples being anionic substances such as fatty acid taurides, fatty acid N-methyltaurides, fatty acid isethionates, alkylbenzenesulfonates, alkylnaphthalenesulfonates, alkylphenol polyglycol ether sulfates and fatty alcohol polyglycol ether sulfates; fatty acids, such as palmitic, stearic and oleic acid; soaps, examples being alkali metal salts of fatty acids, naphthenic acids and resin acids, such as abietic acid, alkali-soluble resins, examples being rosin-modified maleate resins; cationic substances, such as quaternary ammonium salts, fatty amine ethoxylates, fatty amine polyglycol ethers and fatty amines; and nonionic substances, such as fatty alcohol polyglycol ethers, fatty alcohol polyglycol esters and alkylphenol polyglycol ethers.

The pigment preparations of the invention are generally solid systems of flowable pulverulent consistency, or granules.

The dispersing effect which can be obtained in accordance with the invention is assumed to be based on a modification of the surface structure of the base pigments by the pigment dispersants of the formula (IV). Thus in a range of cases the efficacy of the pigment dispersants of the formula (IV) and the quality of the pigment preparations produced with them are dependent on the point in time at which the dispersant is added in the preparation process of the base pigment. The nature of the application of the pigment dispersant of the formula (IV) may also have an influence.

The efficacy of the pigment dispersants of the formula (IV) may also depend on the particle size and particle morphology of the pigment dispersants of the formula (IV) and on the extent of the available pigment surface. It may likewise be advantageous to add the pigment dispersant of the formula (IV) directly to the base pigment only in the prospective application medium. The optimum concentration of the pigment dispersant of the formula (IV) in each case must be determined by means of preliminary guideline experiments, since the enhancement of the properties of the base pigment is not always in linear proportion to the amount of pigment dispersant.

The pigment preparations of the invention can be mixtures of one or more, preferably 1 or 2, base pigments with one or more, preferably 1, 2 or 3, of the pigment dispersants of the formula (IV).

The invention also provides a process for preparing a pigment preparation of the invention, which comprises allowing the pigment dispersant(s) of the formula (IV) and the base pigment(s) to act on one another at any desired point in time during their preparation process.

The preparation process of an organic pigment comprises its synthesis, possible fine division, by milling or reprecipitation, for example, possibly a solvent finish, and its isolation as a presscake, powder or dry granules. For example, the pigment dispersants of the formula (IV) can be added prior to or during the pigment synthesis, prior to or during a process of fine division or prior to or during a subsequent solvent treatment (solvent finish). The temperatures occurring in these processes may be from 0 to 200° C. The pigment dispersant of the formula (IV) can of course also be added in portions at different times.

The addition of the pigment dispersants of the formula (IV) in the course of a process of fine division takes place, for example, in the course of the dry grinding of a crude pigment with or without additional grinding auxiliaries on a roll mill or vibratory mill, or in the course of the wet grinding of a crude pigment in an aqueous, aqueous-organic or organic grinding medium in, for example, a bead mill.

It has also proven suitable to add the pigment dispersants of the formula (IV) prior to or during a finish process for the base pigment in an aqueous, aqueous-alkaline, aqueous-organic or organic medium.

The pigment dispersants of the formula (IV) can also be added to the water-moist pigment presscake prior to drying, and incorporated, in which case the pigment dispersant of the formula (IV) may itself likewise be in the form of a presscake.

It is also possible to make dry mixes of pulverulent pigment dispersants of the formula (IV) with the powder or granules of one or more base pigments.

It is possible, furthermore, to synthesize the pigment dispersant of the formula (IV) and a perylene pigment as a mixture by reaction with the same amine of the formula (IIIa) or (IIIb).

The perylene compounds of the formula (I) of the invention are notable for outstanding fastness properties, such as solvent fastness, and are suitable for use in both solventborne and aqueous systems.

The pigment preparations obtainable in accordance with the present invention are notable for their outstanding coloristic and rheological properties, especially for outstanding rheology, high flocculation stability, high transparency, ease of dispersion, good gloss properties, high color strength, excellent solvent fastness and fastness to overcoating, and very good weather fastness. They are suitable for use in both solventborne and aqueous systems.

The pigment preparations prepared in accordance with the invention can be used for pigmenting (coloring) high molecular mass organic materials of natural or synthetic origin.

Examples of high molecular mass organic materials which can be pigmented with said pigment preparations are cellulose ethers and cellulose esters, such as ethylcellulose, nitrocellulose, cellulose acetate or cellulose butyrate, natural resins and synthetic resins, such as addition-polymerization resins or condensation resins, examples being amino resins, especially urea-formaldehyde and melamine-formaldehyde resins, alkyd resins, acrylic resins, phenolic resins, polycarbonates, polyolefins, such as polystyrene, polyvinyl chloride, polyethylene, polypropylene, polyacrylonitrile, polyacrylates, polyamides, polyurethanes or polyesters, rubber, casein, silicone and silicone resins, individually or in mixtures.

It is irrelevant in this context whether the high molecular mass organic compounds referred to are in the form of plastic masses, melts, spinning solutions, varnishes, paints or printing inks. Depending on the intended application it proves advantageous to utilize the pigment preparations obtained in accordance with the invention as a blend or in the form of preparations or dispersions. Based on the high molecular mass organic material to be pigmented, the pigment preparations of the invention are employed in an amount of preferably from 0.1 to 10% by weight.

The perylene compounds of the formula (I) according to the invention and the pigment preparations of the invention are suitable as colorants in electrophotographic toners and developers, such as one- or two-component powder toners (also called one- or two-component developers), magnetic toners, liquid toners, polymerization toners and specialty toners (L. B. Schein, "Electrophotography and Development Physics"; Springer Series in Electrophysics 14, Springer Verlag, 2nd edition, 1992).

Typical toner binders are addition polymerization, polyaddition and polycondensation resins, such as styrene, styrene-acrylate, styrene-butadiene, acrylate, polyester and phenol-epoxy resins, polysulfones, polyurethanes, individually or in combination, and also polyethylene and polypropylene, which may include further constituents, such as charge control agents, waxes or flow assistants, or may be modified subsequently with these additives.

The perylene compounds of the formula (I) according to the invention and the pigment preparations of the invention are also suitable as colorants in powders and powder coating materials, especially in triboelectrically or electrokinetically sprayable powder coating materials which are used to coat the surfaces of articles made, for example, of metal, wood, plastic, glass, ceramic, concrete, textile material, paper or rubber (J. F. Hughes, "Electrostatics Powder Coating" Research Studies, John Wiley & Sons, 1984).

Typical powder coating resins employed are epoxy resins, carboxyl- and hydroxyl-containing polyester resins, polyurethane resins and acrylic resins, together with customary hardeners. Combinations of resins are also used. For example, epoxy resins are frequently employed in combination with carboxyl- and hydroxyl-containing polyester resins. Typical hardener components (depending on the resin system) are, for example, acid anhydrides, imidazoles and also dicyandiamide and its derivatives, blocked isocyanates, bisacylurethanes, phenolic and melamine resins, triglycidyl isocyanurates, oxazolines and dicarboxylic acids.

Furthermore, the perylene compounds of the formula (I) according to the invention and the pigment preparations of the invention are suitable for use as colorants in inkjet inks on either an aqueous or nonaqueous basis and in those inks which operate in accordance with the hotmelt technique.

It is also possible for the pigment dispersant of the formula (IV) to be added to the base pigment, or vice versa, only in the application medium. The invention therefore also provides a prepared pigment formulation consisting essentially of said base pigment, said pigment dispersant of the formula (IV), said high molecular organic material, especially varnish, if desired surface-active agents, and/or other customary additives. The overall amount of base pigment plus pigment dispersant of the formula (IV) is preferably from 1 to 10% by weight based on the overall weight of the prepared pigment formulation.

To evaluate the properties in the coatings sector of the pigment preparations prepared in accordance with the invention a selection was made from among the large number of known varnishes of an alkyd-melamine resin varnish (AM) containing aromatic components and based on a medium-oil alkyd resin and on a butanol-etherified melamine resin, of a polyester varnish (PE) based on cellulose acetobutyrate and a melamine resin, of a high-solids acrylic resin stoving varnish based on a nonaqueous dispersion (HS), and of a polyurethane-based aqueous varnish (PU).

The color strength and color were determined in accordance with DIN 55986.

The rheology of the millbase after dispersion (millbase rheology) was evaluated visually on the basis of the following five-point scale:
5 highly fluid
4 liquid
3 viscous
2 slightly set
1 set After dilution of the millbase to the final pigment concentration, the viscosity was evaluated with the Rossmann viscospatula, type 301, from Erichsen.

Gloss measurements were carried out on cast films at an angle of 20° in accordance with DIN 67530 (ASTMD 523) using the "multigloss" gloss meter from Byk-Mallinckrodt. The solvent fastness was determined in accordance with DIN 55976. The fastness to overcoating was determined in accordance with DIN 53221. The crystal phase of the pigments and pigment preparations was determined by X-ray spectroscopy. The X-ray spectra were recorded with Cu Kα radiation.

In the examples below, parts and percentages are based in each case on the weight of the substances so described.

EXAMPLE 1

(VIII)

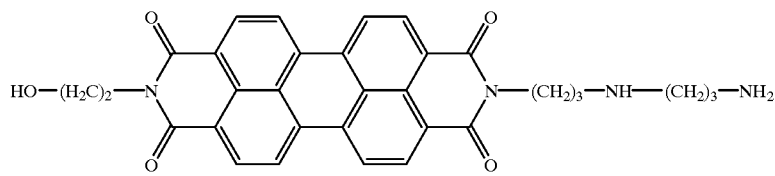

An autoclave is charged with 300 parts of water, 22.7 parts of perylene-3,4,9,10-tetracarboxylic monoanhydride monohydroxyethylimide are introduced, and 26.2 parts of dipropylenetriamine are added. The mixture is subsequently heated under pressure to 150° C. and stirred at 150° C. for 5 hours. After cooling to 25° C., the pigment dispersant is filtered off with suction and washed to neutrality with water.

This gives 143.2 parts of a 19.1% pigment dispersant presscake. Part of this is dried at 80° C. for analysis.

| Analysis: | calc.: 70.1% C |
| | found: 70.0% C |

The $^1$H-NMR spectrum agrees with the structural formula indicated above. δ (D$_2$SO$_4$) 8.65; 6.1; 5.65; 5.16; 4.5; 4.16; 2.97; 2.81; 2.09 and 1.76 ppm.

The solvent fastness of the pigment dispersant is very good.

EXAMPLE 1a

A stirred vessel is charged with 363.5 parts of water, and 108.9 parts of a 20.7% filter cake of perylene-3,4,9,10-tetracarboxylic dianhydride are introduced with stirring. 2.4 parts of a commercial 50% aqueous resin soap are added to this suspension, and 6.2 parts of the 19.1% pigment dispersant presscake of the formula VIII prepared in accordance with Example 1 are introduced. After cooling to 0 to 5° C., 40.8 parts of a 40% strength aqueous monomethylamine solution are added dropwise over 10 minutes. The mixture is stirred at from 0 to 5° C. for a further 15 minutes. Then a solution of 12.8 parts of calcium chloride *2H$_2$O in 42.5 parts of water is added dropwise and the mixture is stirred at from 0 to 5° C. for 1 hour. The suspension is heated to 80° C. and stirred at 80° C. for 2 hours. After cooling to 50° C., acetic acid is added dropwise at this temperature until the pH reaches 8. The resultant pigment preparation is filtered off with suction, washed with water until free from chloride ions and dried in a circulating-air cabinet at 80° C. This gives 27 parts of pigment preparation.

In the HS varnish the pigment preparation gives transparent finishes of high color strength. The rheology is evaluated as 4 and the gloss measurement gives the value 73. The rheology of the PU varnish of the pigment preparation is evaluated as 4.

EXAMPLE 2

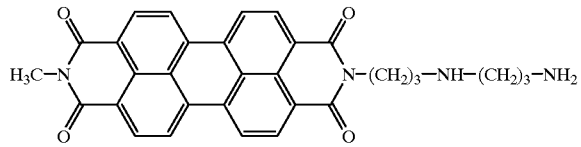

(IX)

An autoclave is charged with 450 parts of water, 37 parts of perylene-3,4,9,10-tetracarboxylic monoanhydride monomethylimide are introduced, and 47.1 parts of dipropylenetriamine are added. The mixture is subsequently heated under pressure to 150° C. and stirred at 150° C. for 5 hours. After cooling to 25° C., the pigment dispersant is filtered off with suction and washed to neutrality with water. This gives 263 parts of a 15.5% pigment dispersant presscake.

| Analysis: | calc.: 12.3% O |
| --- | --- |
|  | found: 13.0% O |

$^1$H-NMR (D$_2$SO$_4$) δ 8.7; 6.1; 5.7; 4.2; 3.5; 3.0; 2.8; 2.0 and 1.8 ppm.

The solvent fastness of the pigment dispersant is very good.

EXAMPLE 2a

A stirred vessel is charged with 3000 parts of water, and 540 parts of a 27.8% filter cake of perylene-3,4,9,10-tetracarboxylic dianhydride are introduced with stirring. 16 parts of a commercial 50% aqueous resin soap are added to this suspension and, after cooling to 0 to 5° C., 222 parts of a 45.4% strength aqueous monomethylamine solution are added dropwise over 10 minutes. The mixture is then stirred at from 0 to 5° C. for 15 minutes. Then a solution of 84.9 parts of anhydrous calcium chloride in 250 parts of water is added dropwise over 15 minutes at from 0 to 5° C. and the mixture is stirred at from 0 to 5° C. for 1 hour. The suspension is heated to 80° C. and stirred at 80° C. for 1 hour. Subsequently, a suspension of 8 parts of distearyldimethylammonium chloride and 350 parts of water is added dropwise and the mixture is stirred at 80° C. for one hour. After cooling to 50° C., 98% formic acid is added dropwise at this temperature until the pH reaches 7. The mixture is stirred at 50° C. for ½ hour, the resultant pigment is filtered off with suction, washed with water until free from chloride ions and dried in a circulating-air cabinet at 80° C. This gives 172.3 parts of pigment (C.I. Pigment Red 179).

20 parts of this pigment are mixed mechanically with 1 part of pigment dispersant of the formula IX prepared in Example 2.

This gives a pigment preparation which in the HS varnish gives transparent finishes of high color strength. The rheology is evaluated as 4. The metallic finish is bright and strongly colored.

Without the addition of the pigment dispersant, the finishes are markedly more hiding and substantially weaker in color. The rheology is evaluated as 1.

EXAMPLE 2b 30 parts of pigment (C.I. Pigment Blue 15:1) are mixed mechanically with 1.5 parts of pigment dispersant of the formula IX prepared in Example 2.

This gives a pigment preparation which in the AM varnish gives transparent finishes of high color strength. The viscosity is 7.0 s. The gloss measurement gives the value 49.

Without the addition of the pigment dispersant the finishes are notably more hiding. The viscosity is 10.3 s. The gloss measurement gives the value 30.

EXAMPLE 2c 30 parts of pigment (C.I. Pigment Red 194) are mixed mechanically with 1.5 parts of pigment dispersant of the formula IX prepared in Example 2.

This gives a pigment preparation which in the AM varnish gives finishes of high color strength. The rheology is evaluated as 4 to 5. The viscosity is 3.3 s. The gloss measurement gives the value 70.

Without the addition of the pigment dispersant the gloss measurement gives the value 60.

EXAMPLE 2d 30 parts of pigment (C.I. Pigment Violet 19) are mixed mechanically with 1.5 parts of pigment dispersant of the formula IX prepared in Example 2.

This gives a pigment preparation which in the AM varnish gives transparent finishes of high color strength with a deep shade. The rheology is evaluated as 5. The viscosity is 5.2 s. The fastness to overcoating is flawless.

Without the addition of the pigment dispersant the finishes are notably more hiding and markedly paler.

EXAMPLE 2e 30 parts of pigment (C.I. Pigment Red 168) are mixed mechanically with 0.75 part of pigment dispersant of the formula IX prepared in Example 2.

This gives a pigment preparation which in the AM varnish gives transparent finishes of high color strength with a deep shade. The rheology is evaluated as 4 to 5. The viscosity is 3.2 s.

Without the addition of the pigment dispersant the finishes are notably more hiding and substantially paler.

EXAMPLE 2f 30 parts of pigment (C.I. Pigment Violet 23) are mixed mechanically with 1.5 parts of pigment dispersant of the formula IX prepared in Example 2.

This gives a pigment preparation which in the AM varnish gives finishes of high color strength. The rheology is evaluated as 3. The viscosity is 4.6 s.

Without the addition of the pigment dispersant the viscosity is 5.1 s.

EXAMPLE 2g

A steel container filled to 80% of its volume with 1400 parts of steatite balls with a diameter of 12 mm as grinding media is charged with 30 parts of coarsely crystalline crude perylene pigment (C.I. Pigment Red 149) (prepared in accordance with DE-C 1 067 157), 150 parts of anhydrous sodium sulfate and 1.6 parts of pigment dispersant of the formula IX prepared in Example 2 and this charge is milled in a vibratory mill (type: Vibratom, manufacturer: Siebtechnik, Mühlheim) at 1400 revolutions per minute for 8 hours with a vibration circle of 4 mm. The millbase is then screened to remove the grinding media. The millbase is introduced into 1500 parts of water and stirred at 80° C. for 1 hour. The pigment preparation is then filtered off with suction, washed with water until salt-free and dried at 80° C. This gives 28.6 parts of pigment preparation.

In the AM varnish the pigment preparation gives transparent finishes of high color strength. The viscosity is 12.9 s.

Without the addition of the pigment dispersant the finishes are markedly more hiding. The viscosity is so high that it cannot be measured with the viscospatula.

EXAMPLE 2h 30 parts of pigment (C.I. Pigment Brown 25) are mixed mechanically with 1.5 parts of pigment dispersant of the formula IX prepared in Example 2.

This gives a pigment preparation which gives finishes of high color strength in the AM varnish. The viscosity is 6.8 s. The gloss measurement gives the value 63.

Without the addition of the pigment dispersant the viscosity is 8.5 s. The gloss measurement gives the value 59.

In the PE varnish the pigment preparation gives transparent finishes of high color strength with flawless fastness to overcoating. The metallic finish is bright and strongly colored.

Without the addition of the pigment dispersant the finishes are more hiding.

EXAMPLE 2i

Ring closure and hydrolysis:

150 parts of 2,5-dianilinoterephthalic acid are introduced with stirring at from 80 to 90° C. into 750 parts of polyphosphoric acid containing >84% $P_2O_5$ and are heated to 125° C. for 1 hour during which ring closure takes place to form the quinacridone. Thereafter, the reaction mixture is hydrolyzed with 3375 parts of 13.9% phosphoric acid with stirring at a temperature of 80° C. The mixture is stirred at 105° C. for 1 hour. Subsequently, the crude pigment is filtered off with suction and washed to neutrality. This gives 734 parts of an 18.0% crude pigment filtercake present predominantly in the α phase.

Phase conversion:

694.5 parts of the crude pigment filtercake are introduced into a stirred vessel, 680.5 parts of water, 12.9 parts of 98% sodium hydroxide and 375 parts of 100% isobutanol are added, and the mixture is heated under pressure to 150° C. and stirred at 150° C. for 5 hours. After cooling to 90° C., the isobutanol is distilled off azeotropically at up to 100° C. at the bridge. The suspension is cooled to 60° C. and the crude pigment is filtered off with suction, washed to neutrality with water and dried at 80° C.

This gives 115.7 parts of highly crystalline crude pigment which is present in the β-phase.

Milling:

A suspension consisting of 77 parts of 1% sodium hydroxide, 6.3 parts of coarsely crystalline crude unsubstituted quinacridone pigment (β phase) and 0.32 part of pigment dispersant of the formula IX prepared in Example 2 is metered into a stirred ball mill (manufacturer: Draiswerke GmbH, Mannheim) filled with 360 parts of zirconium mixed oxide beads of diameter 0.3–0.4 mm as grinding media and milled at 25° C. for 15 minutes with a stirrer tip speed (peripheral stirrer speed) of 15.6 m/s and a specific power density of 3.1 kW per liter of milling space. This milling is carried out a second time, and the two millbase suspensions are combined and screened to remove the grinding media, which are rinsed off with water. The millbase suspensions are subsequently filtered with suction and the solid products are washed with water and dried at 80° C.

This gives 11.9 parts of pigment preparation based on C.I. Pigment Violet 19 which in the AM varnish gives transparent finishes of high color strength and deep shade. The rheology is evaluated as 5. The viscosity is 3.7 s. The fastness to overcoating is flawless.

Without the addition of the pigment dispersant, the finishes are substantially paler and markedly more hiding.

EXAMPLE 2j 30 parts of pigment (C.I. Pigment Red 122) are mixed mechanically with 0.7 part of pigment dispersant of formula IX prepared in accordance with Example 2. This gives a pigment preparation which in the AM varnish gives transparent finishes of high color strength with a deep shade. The rheology is evaluated as 4 to 5. The gloss measurement gives the value 55. The fastness to overcoating is flawless. Without the addition of the pigment dispersant the finishes are notably more hiding and markedly paler.

EXAMPLE 3

15 parts of pigment (C.I. Pigment Red 179) prepared in accordance with Example 2a are mixed mechanically with 0.75 part of pigment dispersant of the formula VIII prepared in accordance with Example 1 and with 0.75 part of pigment dispersant of the formula IX prepared in accordance with Example 2.

This gives a pigment preparation whose solvent fastness is very good. In the HS varnish the pigment preparation gives transparent finishes of high color strength. The rheology is evaluated as 4 and the viscosity is 2.0 s. The gloss measurement gives the value 69.

Without the addition of the two pigment dispersants, the finishes of the HS varnish are weaker in color and substantially more hiding. The rheology is evaluated as 1 and the viscosity is so high that it cannot be measured with the viscospatula. The gloss cannot be measured because of the severe flocculation.

In the PU varnish the pigment preparation gives transparent finishes and the rheology is evaluated as 4.

Without the addition of the two pigment dispersants, the finishes of the PU varnish are notably more hiding. The rheology is evaluated as 3 to 4.

EXAMPLE 4

(X)

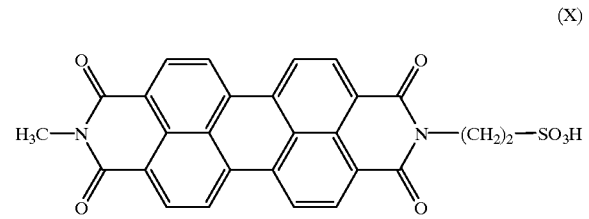

An autoclave is charged with 1200 parts of water, and 50.1 parts of taurine are introduced and dissolved. A pH of 9.6 is established in this solution by further addition of 26.4 parts of potassium hydroxide (85%). Subsequently, 40.5 parts of perylene-3,4,9,10-tetracarboxylic monoanhydride N-monomethylimide are introduced. The mixture is heated to 150° C. and stirred at 150° C. for 3 hours. After cooling to 25° C., the reaction product formed as the potassium salt is filtered off with suction, washed with water and dried at 80° C. The residue obtained is introduced initially at 25° C. in 1000 parts of 100% sulfuric acid and is dissolved. Subsequently, 850 parts of 50% sulfuric acid are added dropwise to this solution, in the course of which the temperature is allowed to rise to 80° C. The mixture is subsequently cooled to 25° C. and the sulfonic acid liberated in this way is filtered off with suction, washed with 78% sulfuric acid, then washed with 31% hydrochloric acid until free of sulfate, and dried under reduced pressure at 80° C.

This gives 44.9 parts of pigment dispersant of the formula X containing 1.9% chemically bound water, corresponding to 44.0 parts at 100% purity (=85.9% of theory).

| Analysis: Taking into account 1.9% of water |
|---|
| Calc: 63.3% C |
| Found: 63.0% C |

EXAMPLE 4a 100 parts of pigment (C.I. Pigment Red 179) prepared in accordance with Example 2a are mixed mechanically with 10 parts of pigment dispersant of the formula IX prepared in accordance with Example 2, and with 5 parts of pigment dispersant of the formula X prepared in accordance with Example 4 and with 1 part of commercial C.I. Basic Blue 140.

This gives a pigment preparation whose solvent fastness is very good. In the HS varnish, the pigment preparation gives transparent finishes with high color strength. The rheology is evaluated as 4 to 5 and the viscosity is 1.7 s. The gloss measurement gives the value 68. The metallic finish is strongly colored and bright.

Without the addition of the two pigment dispersants the finishes are weaker in color and more hiding. The rheology is evaluated as 1 and the viscosity is so high that it cannot be measured with the Viskospatula. The gloss as well cannot be measured owing to the severe flocculation. The metallic finish is weakly colored and matt.

EXAMPLE 5

A stirred vessel is charged with 2000 parts of water, and 90 parts of perylene-3,4,9,10-tetracarboxylic dianhydride and 31 parts of 15.5% presscake of the pigment dispersant of the formula IX prepared in accordance with Example 2 are introduced with stirring. 9.6 parts of a commercial 50% aqueous resin soap are added to this suspension and after cooling to 0 to 5° C., 163 parts of a 40% strength aqueous monomethylamine solution are added dropwise over 10 minutes. The mixture is then stirred at from 0 to 5° C. for a further 15 minutes. Then a solution of 51 parts of calcium chloride *2H$_2$O in 170 parts of water is added dropwise and the mixture is stirred at from 0 to 5° C. for 1 hour. The suspension is heated to 80° C. and stirred at 80° C. for 1 hour. Then a suspension of 4.8 parts of distearyldimethylammonium chloride and 280 parts of water is added dropwise and the mixture is stirred at 80° C. for one hour. After cooling to 50° C., acetic acid is added dropwise at this temperature until the pH reaches 8. The resultant pigment preparation is filtered off with suction, washed with water until free from chloride ions and dried in a circulating-air cabinet at 80° C.

This gives 106.9 parts of pigment preparation.

10 parts of the above pigment preparation are mixed mechanically with 0.42 part of pigment dispersant of the formula IX prepared in accordance with Example 2 and with 0.42 part of pigment dispersant of formula X prepared in accordance with Example 4 and with 0.04 part of commercial C.I. Basic Blue 140.

This gives a pigment preparation whose solvent fastness is very good. In the HS varnish, the pigment preparation gives transparent finishes with high color strength. The rheology is evaluated as 5 and the viscosity is 3.0 s. The gloss measurement gives the value 71. The metallic finish is strongly colored and bright.

Without the addition of the two pigment dispersants the finishes are weaker in color and more hiding. The rheology is evaluated as 1 and the viscosity is so high that it cannot be measured with the viscospatula. The gloss as well cannot be measured owing to the severe flocculation. The metallic finish is weakly colored and matt.

EXAMPLE 6

(XI)

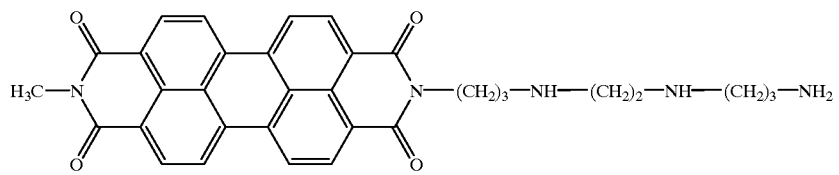

An autoclave is charged with 500 parts of water, 40.5 parts of perylene-3,4,9,10-tetracarboxylic monoanhydride monomethylimide are introduced, and 52.2 parts of N,N'-bis(3-aminopropyl)ethylenediamine are added. The mixture is subsequently heated under pressure to 150° C. and stirred at 150° C. for 5 hours. After cooling to 25° C., the pigment dispersant is filtered off with suction and washed to neutrality with water. This gives 132.2 parts of a 34.8% pigment dispersant presscake.

| Analysis: | calc.: 70.6% C |
|---|---|
| | found: 71.1% C |

$^1$H-NMR (D$_2$SO$_4$): δ 8.71; 6.32; 5.71; 4.47; 4.17; 3.51; 3.3; 3.0; 2.08 ppm.

The solvent fastness of the pigment dispersant is very good.

EXAMPLE 6a

A stirred vessel is charged with 368 parts of water, and 104.5 parts of a 21.5% filter cake of perylene-3,4,9,10-tetracarboxylic dianhydride are introduced with stirring. 2.4 parts of a commercial 50% aqueous resin soap are added to this suspension and after cooling to 0–5° C., 40.8 parts of a 40% strength aqueous monomethylamine solution are added dropwise over 10 minutes. The mixture is stirred at from 0 to 5° C. for a further 15 minutes. Then a solution of 12.8 parts of calcium chloride *$2H_2O$ in 42.5 parts of water is added dropwise at from 0 to 5° C. for 1 hour. The suspension is heated to 80° C. and stirred at 80° C. for 1 hour. Subsequently, a suspension of 3.44 parts of a 34.8% pigment dispersant presscake of the formula XI prepared in accordance with Example 6 and 50 parts of water is added and the mixture is stirred at 80° C. for one hour. After cooling to 60° C., acetic acid is added dropwise at this temperature until the pH reaches 8. The resultant pigment is filtered off with suction, washed with water until free from chloride ions and dried in a circulating-air cabinet at 80° C.

This gives 26.3 parts of pigment preparation.

In the HS varnish the pigment preparation gives transparent finishes of high color strength. The rheology is evaluated as 4 and the viscosity is 3.1 s. The gloss measurement gives the value 74.

If instead of the 5.5 parts of a 34.8% pigment dispersant presscake of the formula XI prepared in accordance with Example 6 a suspension of 1.2 parts of distearyldimethylammonium chloride and 70 parts of water are added dropwise, the finishes are notably more hiding and substantially weaker in color. The rheology is evaluated as 1 and the viscosity is so high that it cannot be measured with the viscospatula. The gloss as well cannot be measured owing to the severe flocculation.

EXAMPLE 6b 10 parts of pigment preparation prepared in accordance with Example 6a are mixed mechanically with 0.45 part of pigment dispersant of the formula IX prepared in accordance with Example 2.

In the HS varnish the pigment preparation gives transparent finishes of high color strength. The rheology is evaluated as 4 to 5. The viscosity is 1.2 s. The gloss measurement gives the value of 72. The metallic finish is strongly colored and bright.

If instead of the 5.5 parts of a 34.8% pigment dispersant presscake of the formula XI prepared in accordance with Example 6 a suspension of 1.2 parts of distearyldimethylammonium chloride and 70 parts of water are added dropwise and, in addition, no mechanical mixing with 0.45 part of pigment dispersant of the formula IX prepared in accordance with Example 2 is carried out, the rheology is evaluated as 1. The viscosity is so high that it cannot be measured with the viscospatula. The gloss as well cannot be measured owing to the severe flocculation. The metallic finish is weakly colored and matt.

EXAMPLE 7

30 parts of pigment (C.I. Pigment Red 179) prepared in accordance with Example 2a are mixed mechanically with 1.35 parts of pigment dispersant of the formula IX prepared in accordance with Example 2.

This gives a pigment preparation whose solvent fastness is very good. In the PE3 varnish, the pigment preparation gives finishes of high color strength with a deep shade. The viscosity is 2.8 s. The fastness to overcoating is flawless.

Without the addition of the pigment dispersant, the finishes are paler and the viscosity is 3.8 s.

In the PUR varnish, the pigment preparation gives transparent finishes of high color strength with a deep shade, and the rheology is evaluated as 3 to 4.

Without the addition of the pigment dispersant, the finishes are more hiding and paler, and the rheology is evaluated as 3.

EXAMPLE 8

30 parts of pigment (C.I. Pigment Red 179) prepared in accordance with Example 2a are mixed mechanically with 1.35 parts of pigment dispersant of the formula VIII prepared in accordance with Example 1 and with 1.35 parts of pigment dispersant of the formula IX prepared in accordance with Example 2.

This gives a pigment preparation which in the PE varnish gives finishes of high color strength with a deep shade. The viscosity is 2.6 s. The fastness to overcoating is flawless.

Without the addition of the pigment dispersant, the finishes are paler and the viscosity is 3.8 s.

In the PUR varnish, the pigment preparation gives transparent finishes with a deep shade, and the rheology is evaluated as 3 to 4.

Without the addition of the pigment dispersant, the finishes are markedly more hiding and substantially paler, and the rheology is evaluated as 3.

EXAMPLE 9 (COMPARATIVE EXAMPLE)

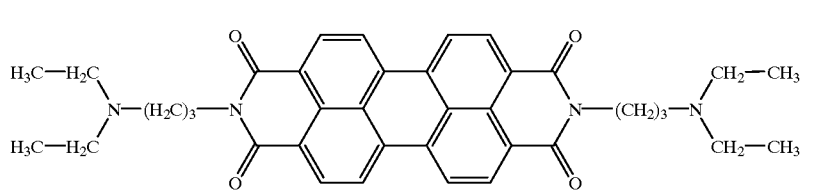

(XII)

An autoclave is charged with 500 parts of water, 189.7 parts of a 20.7% filtercake of perylene-3,4,9,10-tetracarboxylic dianhydride are introduced, and 52 parts of diethylaminopropylamine are added. The mixture is subsequently heated under pressure to 150° C. and stirred at 150° C. for 5 hours. After cooling to 25° C., the pigment dispersant is filtered off with suction and washed to neutrality with water. This gives 138.2 parts of a 45.2% pigment dispersant presscake.

| Analysis: | calc.: 9.1% N |
|---|---|
| | found: 9.1% N |

$^1$H-NMR spectrum (D$_2$SO$_4$): δ 8.7; 4.1; 2.87; 2.8; 1.9 and 0.9 ppm.

The solvent fastness of the pigment dispersant is inadequate. In comparison to the solvent fastness of the pigment dispersant of the formula VIII prepared in accordance with Example 1, of the pigment dispersant of the formula IX prepared in accordance with Example 2 and of the pigment dispersant of the formula XI prepared in accordance with Example 6, it is substantially poorer and hence markedly inferior.

be measured since the cast films likewise do not cure. The rheology is evaluated as 3 to 4.

In contrast, the pigment preparation of Example 2a (instead of 1 part of pigment dispersant of the formula XII prepared in accordance with Example 9, 1 part of pigment dispersant of the formula IX prepared in accordance with Example 2 was used for mechanical mixing) in the HS varnish gives transparent finishes of high color strength which cure flawlessly on stoving. The rheology is evaluated as 4.

The deficiencies indicated show that the pigment preparation of Example 2a is markedly superior.

EXAMPLE 10

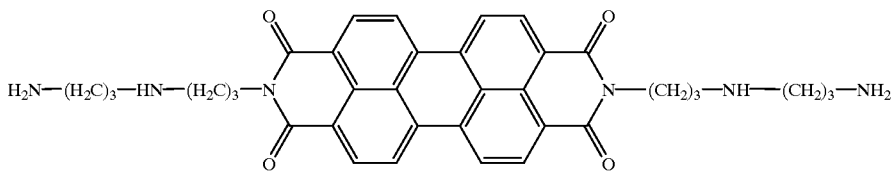

(XIII)

EXAMPLE 9a (COMPARATIVE EXAMPLE)

30 parts of pigment (C.I. Pigment Red 179) prepared in accordance with Example 2a are mixed mechanically with 1.35 parts of pigment dispersant of the formula XII prepared in accordance with Example 9.

This gives a pigment preparation which in the HS varnish gives masstone finishes which no longer cure fully on stoving. The gloss cannot be measured since the cast films likewise do not cure. The metallic finish as well does not cure. The rheology is evaluated as 3.

In the AM varnish the fastness to overcoating is inadequate.

In contrast, the pigment preparation of Example 7 (instead of 1.35 parts of pigment dispersant of the formula XII prepared in accordance with Example 9, 1.35 parts of pigment dispersant of the formula IX prepared in accordance with Example 2 were used for mechanical mixing) in the HS varnish gives transparent finishes of high color strength which cure flawlessly on stoving. The gloss measurement gives the value 77. The metallic finish is bright and strongly colored. The rheology is evaluated as 4.

The fastness to overcoating in the AM varnish of the finish of the pigment preparation of Example 7 is also notably better.

The deficiencies indicated show that the pigment preparation of Example 7 is markedly superior.

EXAMPLE 9b (COMPARATIVE EXAMPLE)

20 parts of pigment (C.I. Pigment Red 179) prepared in accordance with Example 2a are mixed mechanically with 1 part of pigment dispersant of the formula XII prepared in accordance with Example 9.

This gives a pigment preparation whose solvent fastness is inadequate. It is substantially poorer in comparison to the solvent fastnesses of the pigment preparations of Examples 3, 4a and 5 and is therefore markedly inferior.

In the HS varnish the pigment preparation gives masstone finishes which do not cure fully on stoving. The gloss cannot An autoclave is charged with 300 parts of water, 189.7 parts of a 20.7% filtercake of perylene-3,4,9,10-tetracarboxylic dianhydride are introduced, and 104.8 parts of 3,3'-iminobispropylamine are added. The mixture is subsequently heated under pressure to 150° C. and stirred at 150° C. for 5 hours. After cooling to 25° C., the pigment dispersant is filtered off with suction and washed to neutrality with water.

This gives 435.3 parts of a 12.5% pigment dispersant presscake.

| Analysis: | calc.: 69.9% C |
|---|---|
| | found: 68.2% C |

$^1$H-NMR spectrum (D$_2$SO$_4$): δ 8.67; 6.03; 5.65; 4.15; 2.95; 2.8; 1.95 and 1.75 ppm.

EXAMPLE 10a

A stirred vessel is charged with 36.5 parts of water, and 108.9 parts of a 20.7% filtercake of perylene-3,4,9,10-tetracarboxylic dianhydride and 9.6 parts of 12.5% presscake of the pigment dispersant of the formula XIII prepared in accordance with Example 10 are introduced with stirring. 2.4 parts of a commercial 50% aqueous resin soap are added to this suspension and after cooling to 0 to 5° C., 40.8 parts of a 40% strength aqueous monomethylamine solution are added dropwise over 10 minutes. The mixture is stirred at from 0 to 5° C. for a further 15 minutes. Then a solution of 12.8 parts of calcium chloride *2H$_2$O in 42.5 parts of water is added dropwise and the mixture is stirred at from 0 to 5° C. for 1 hour. The suspension is heated to 80° C. and stirred at 80° C. for 1 hour. Then a suspension of 1.2 parts of distearyldimethylammonium chloride and 70 parts of water is added dropwise and the mixture is stirred at 80° C. for one hour. After cooling to 50° C., acetic acid is added dropwise at this temperature until the pH reaches 8. The resultant pigment preparation is filtered off with suction, washed with water until free from chloride ions and dried in a circulating-air cabinet at 80° C.

This gives 27.6 parts of pigment preparation.

In the HS varnish the pigment preparation gives transparent finishes of high color strength. The rheology is evaluated as 3 to 4 and the viscosity is 13.6 s. The gloss measurement gives the value 38.

Without the addition of the pigment dispersant the finishes are markedly weaker in color and notably more hiding. The rheology is evaluated as 1 and the viscosity is so high that it cannot be measured with the Viskospatula. The gloss as well cannot be measured, owing to the severe flocculation.

EXAMPLE 11 evaluated as 3 to 4 and the gloss measurement gives the value 59. The viscosity is 4.8 s.

EXAMPLE 11b 10 parts of pigment preparation prepared in accordance with Example 11a are mixed mechanically with 0.45 part of pigment dispersant of the formula IX prepared in accordance with Example 2.

This gives a pigment preparation which in the HS varnish gives transparent finishes of high color strength. The rheology is evaluated as 4 and the gloss measurement gives the value 70. The viscosity is 1.2 s.

(XIV)

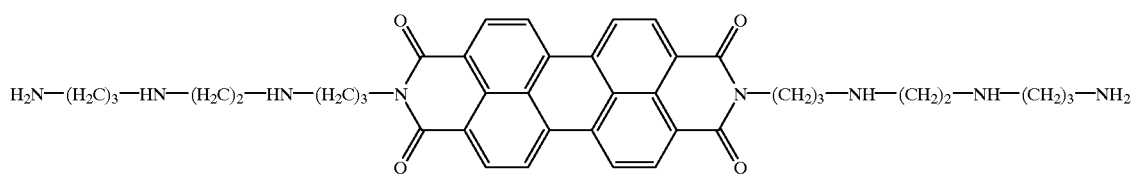

An autoclave is charged with 500 parts of water, 181.9 parts of a 21.5% filtercake of perylene-3,4,9,10-tetracarboxylic dianhydride are introduced, and 69.6 parts of N,N'-bis(3-aminopropyl)ethylenediamine are added. The mixture is subsequently heated under pressure to 150° C. and stirred at 150° C. for 5 hours. After cooling to 25° C., the pigment dispersant is filtered off with suction and washed to neutrality with water. This gives 390.2 parts of a 12.9% pigment dispersant presscake.

| Analysis: | calc.: 68.2% C |
| | found: 67% C |

$^1$H-NMR spectrum (D$_2$SO$_4$): δ 8.7; 6.3; 5.7; 4.2; 3.3; 3.1; 2.95; 2.85; 2.1 and 1.82 ppm.

EXAMPLE 11a

A stirred vessel is charged with 368 parts of water, and 104.5 parts of a 21.5% filtercake of perylene-3,4,9,10-tetracarboxylic dianhydride are introduced with stirring. 2.4 parts of a commercial 50% aqueous resin soap are added to this suspension and 9.3 parts of a 12.9% pigment dispersant presscake of the formula XIV prepared in accordance with Example 11 are introduced. After cooling to 0 to 5° C., 40.8 parts of a 40% strength aqueous monomethylamine solution are added dropwise over 10 minutes. The mixture is stirred at from 0 to 5° C. for a further 15 minutes. Then a solution of 12.8 parts of calcium chloride *2H$_2$O in 42.5 parts of water is added dropwise and the mixture is stirred at from 0 to 5° C. for 1 hour. The suspension is heated to 80° C. and stirred at 80° C. for 2 hours. After cooling to 60° C., acetic acid is added dropwise at this temperature until the pH reaches 8. The resultant pigment preparation is filtered off with suction, washed with water until free from chloride ions and dried in a circulating-air cabinet at 80° C.

This gives 26 parts of pigment preparation.

In the HS varnish the pigment preparation gives transparent finishes of high color strength. The rheology is

EXAMPLE 12

(XV)

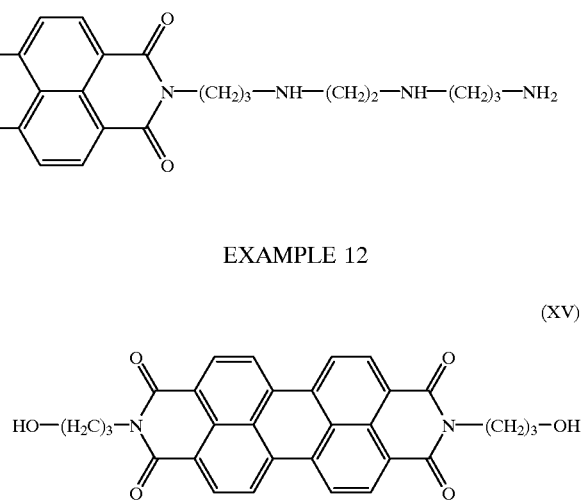

An autoclave is charged with 500 parts of water, 181.9 parts of a 21.5% filtercake of perylene-3,4,9,10-tetracarboxylic dianhydride are introduced, and 30 parts of 3-amino-1-propanol are added. The mixture is subsequently heated under pressure to 150° C. and stirred at 150° C. for 5 hours. After cooling to 25° C., the pigment dispersant is filtered off with suction and washed to neutrality with water. This gives 118 parts of a 43.1% pigment dispersant presscake.

Analysis:
  calc.: 71.1 % C
  found: 70.8 % C
  $^1$H-NMR spectrum (D$_2$SO$_4$): δ 8.67; 4.7; 4.2; 3.9; 2.15 and 2.0 ppm.

The solvent fastness of the pigment dispersant is very good.

EXAMPLE 12a

A stirred vessel is charged with 368 parts of water, and 104.5 parts of a 21.5% filtercake of perylene-3,4,9,10-tetracarboxylic dianhydride are introduced with stirring. 2.4 parts of a commercial 50% aqueous resin soap are added to this suspension and after cooling to 0 to 5° C., 40.8 parts of a 40% strength aqueous monomethylamine solution are added dropwise over 10 minutes. The mixture is stirred at from 0 to 5° C. for a further 15 minutes. Then a solution of 12.8 parts of calcium chloride *2H$_2$O in 42.5 parts of water is added dropwise and the mixture is stirred at from 0 to 5°

C. for 1 hour. The suspension is heated to 80° C. and stirred at 80° C. for 1 hour. Thereafter, a suspension of 2.78 parts of a 43.1% pigment dispersant presscake of the formula XV prepared in accordance with Example 12 and 50 parts of water are added and the mixture is stirred at 80° C. for one hour. After cooling to 60° C., acetic acid is added dropwise at this temperature until the pH reaches 8. The resultant pigment preparation is filtered off with suction, washed with water until free from chloride ions and dried in a circulating-air cabinet at 80° C. In the HS varnish the pigment preparation gives transparent finishes of high color strength. The rheology is evaluated as 4 to 5.

EXAMPLE 12b 10 parts of pigment preparation prepared in accordance with Example 12a are mixed mechanically with 0.45 part of pigment dispersant of the formula IX prepared in accordance with Example 2.

This gives a pigment preparation which in the HS varnish gives transparent finishes of high color strength. The rheology is evaluated as 4 and the gloss measurement gives the value 67. The viscosity is 1.8 s.

EXAMPLE 13

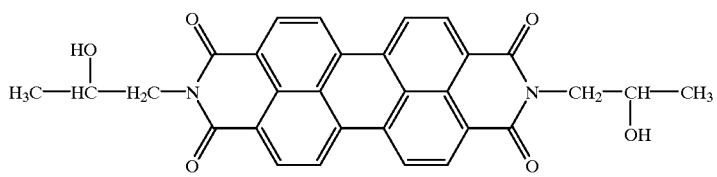

(XVI)

An autoclave is charged with 500 parts of water, 181.9 parts of a 21.5% filtercake of perylene-3,4,9,10-tetracarboxylic dianhydride are introduced, and 30 parts of 1-amino-2-propanol are added. The mixture is subsequently heated under pressure to 150° C. and stirred at 150° C. for 5 hours. After cooling to 25° C., the pigment dispersant is filtered off with suction and washed to neutrality with water. This gives 139.8 parts of a 35.8% pigment dispersant presscake.

| Analysis: | calc.: 71.1% C |
| --- | --- |
| | found: 70.9% C |

$^1$H-NMR spectrum ($D_2SO_4$): δ 8.67; 5.6; 4.45; 3.9 and 1.5 ppm.

The solvent fastness of the pigment dispersant is very good.

EXAMPLE 13a 15 parts of pigment (C.I. Pigment Red 179) prepared in accordance with Example 2a are mixed mechanically with 0.75 part of pigment dispersant of the formula IX prepared in accordance with Example 2 and with 0.75 part of pigment dispersant of the formula XVI prepared in accordance with Example 13.

This gives a pigment preparation which in the HS varnish gives transparent finishes of high color strength. The rheology is evaluated as 4 and the gloss measurement gives the value 73. The viscosity is 1.8 s.

EXAMPLE 14

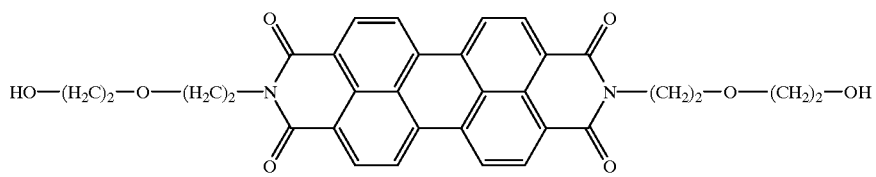

(XVII)

An autoclave is charged with 500 parts of water, 181.9 parts of a 21.5% filtercake of perylene-3,4,9,10-tetracarboxylic dianhydride are introduced, and 42 parts of 2-(2-aminoethoxy)ethanol are added. The mixture is subsequently heated under pressure to 150° C. and stirred at 150° C. for 5 hours. After cooling to 25° C., the pigment dispersant is filtered off with suction and washed to neutrality with water. This gives 161.7 parts of a 38.4% pigment dispersant presscake.

| Analysis: | calc.: 4.9% N |
| --- | --- |
| | found: 4.9% N |

$^1$H-NMR spectrum ($D_2SO_4$): δ 8.7; 5.25; 4.45 and 4.3 ppm.

The solvent fastness of the pigment dispersant is very good.

EXAMPLE 14a

A stirred vessel is charged with 366.5 parts of water, and 106 parts of a 21.3% filtercake of perylene-3,4,9,10-tetracarboxylic dianhydride are introduced with stirring. 2.4 parts of a commercial 50% aqueous resin soap are added to this suspension and 3.12 parts of a 38.4% pigment dispersant presscake of the formula XVII prepared in accordance with Example 14 are introduced. After cooling to 0 to 5° C., 40.8 parts of a 40% strength aqueous monomethylamine solution are added dropwise over 10 minutes. The mixture is stirred at from 0 to 5° C. for a further 15 minutes. Then a solution of 12.8 parts of calcium chloride *2H$_2$O in 42.5 parts of water is added dropwise and the mixture is stirred at from 0 to 5° C. for 1 hour. The suspension is heated to 80° C. and stirred at 80° C. for 2 hours. After cooling to 60° C., acetic acid is added dropwise at this temperature until the pH reaches 8. The resultant pigment preparation is filtered off with suction, washed with water until free from chloride ions and dried in a circulating-air cabinet at 80° C.

This gives 25.3 parts of pigment preparation.

In the HS varnish the pigment preparation gives transparent finishes of high color strength. The rheology is evaluated as 3 to 4.

EXAMPLE 15

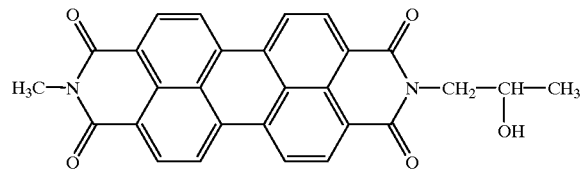

(XVIII)

An autoclave is charged with 900 parts of water, 40.5 parts of perylene-3,4,9,10-tetracarboxylic monoanhydride monomethylimide are introduced, and 30 parts of 1-amino-2-hydroxypropane are added. The mixture is subsequently heated under pressure to 150° C. and stirred at 150° C. for 5 hours. After cooling to 25° C., the pigment dispersant is filtered off with suction and washed to neutrality with water. This gives 117.7 parts of a 38% pigment dispersant presscake. A portion is dried at 80° C. for analysis and for mechanical mixtures.

| Analysis: | calc.: 6.1% N |
|---|---|
|  | found: 6.1% N |

$^1$H-NMR spectrum (D$_2$SO$_4$): δ 8.7; 5.7; 4.5; 4.0; 3.5 and 1.5 ppm.

The solvent fastness of the pigment dispersant is very good.

EXAMPLE 15a 10 parts of pigment (C.I. Pigment Red 179) prepared in accordance with Example 2a are mixed mechanically with 0.45 part of pigment dispersant of the formula XVIII prepared in accordance with Example 15.

This gives a pigment preparation which in the HS varnish gives transparent finishes of high color strength.

EXAMPLE 16

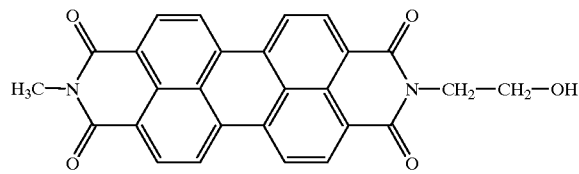

(XIX)

An autoclave is charged with 300 parts of water, 22.7 parts of perylene-3,4,9,10-tetracarboxylic monoanhydride monohydroxyethylimide are introduced, and 15.5 parts of a 40% strength aqueous monomethylamine solution are added. The mixture is subsequently heated under pressure to 150° C. and stirred at 150° C. for 5 hours. After cooling to 25° C., the pigment dispersant is filtered off with suction and washed to neutrality with water. This gives 66.2 parts of a 35.1% pigment dispersant presscake. A portion is dried at 80° C. for analysis and for mechanical mixtures.

| Analysis: | calc.: 72.3% C |
|---|---|
|  | found: 72.1% C |

$^1$H-NMR spectrum (D$_2$SO$_4$): δ 8.7; 5.16; 4.5; 4.41 and 3.48 ppm.

The solvent fastness of the pigment dispersant is very good.

EXAMPLE 16a 20 parts of pigment (C.I. Pigment Red 179) prepared in accordance with Example 2a are mixed mechanically with 1 part of pigment dispersant of the formula XIX prepared in accordance with Example 16.

This gives a pigment preparation which in the HS varnish gives transparent finishes of high color strength.

EXAMPLE 17

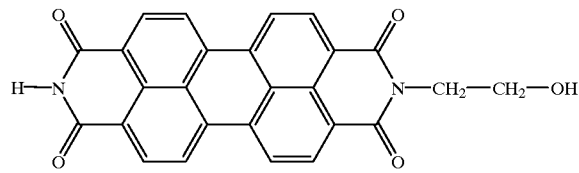

(XX)

An autoclave is charged with 300 parts of water, 22.7 parts of perylene-3,4,9,10-tetracarboxylic monoanhydride monohydroxyethylimide are introduced, and 13.2 parts of a 25% strength aqueous ammonia solution are added. The mixture is subsequently heated under pressure to 150° C. and stirred at 150° C. for 5 hours. After cooling to 25° C., the pigment dispersant is filtered off with suction and washed to neutrality with water.

This gives 68.7 parts of a 32.2% pigment dispersant presscake. A portion is dried at 80° C. for analysis.

| Analysis: | calc.: 71.9% C |
|---|---|
|  | found: 71.8% C |

$^1$H-NMR spectrum (D$_2$SO$_4$): δ 8.7; 5.2; 4.53 and 4.45 ppm.

The solvent fastness of the pigment dispersant is very good.

EXAMPLE 17a

A stirred vessel is charged with 363.5 parts of water, and 108.9 parts of a 20.7% filtercake of perylene-3,4,9,10-tetracarboxylic dianhydride are introduced with stirring. 2.4 parts of a commercial 50% aqueous resin soap are added to this suspension and 3.72 parts of a 32.2% pigment dispersant presscake of the formula XX prepared in accordance with Example 17 are introduced. After cooling to 0 to 5° C., 40.8 parts of a 40% strength aqueous monomethylamine solution are added dropwise over 10 minutes. The mixture is stirred at from 0 to 5° C. for a further 15 minutes. Then a solution of 12.8 parts of calcium chloride *2H$_2$O in 42.5 parts of water is added dropwise and the mixture is stirred at from 0 to 5° C. for 1 hour. The suspension is heated to 80° C. and stirred at 80° C. for 2 hours. After cooling to 60° C., acetic acid is added dropwise at this temperature until the pH reaches 8. The resultant pigment preparation is filtered off with suction, washed with water until free from chloride ions and dried in a circulating-air cabinet at 80° C.

This gives 27.4 parts of pigment preparation.

In the HS varnish the pigment preparation gives transparent finishes of high color strength.

EXAMPLE 18

A stirred vessel is charged with 400 parts of o-dichlorobenzene, 40.5 parts of perylene-3,4,9,10-tetracarboxylic monoanhydride monomethylimide are introduced, and 52.4 parts of 3,3'-iminobispropylamine are added. The mixture is subsequently heated to 150° C. and stirred at 150° C. for 5 hours. After cooling to 25° C., the pigment dispersant is filtered off with suction and washed with o-dichlorobenzene until the runnings are clear. The presscake is stirred up in water and residual o-dichlorobenzene is removed by steam distillation. The pigment dispersant is filtered off with suction, washed with water and dried at 80° C.

This gives 40.1 parts of pigment dispersant of the formula IX.

| Analysis: | calc.: 72% C |
|---|---|
|  | found: 73% C |

The $^1$H-NMR spectrum agrees with the structural formula indicated above, the signals lying at a shift of 8.7 ppm, 6.1 ppm, 5.7 ppm, 4.2 ppm, 3.5 ppm, 3.0 ppm, 2.8 ppm, 2.0 ppm and 1.8 ppm.

EXAMPLE 18a 10 parts of pigment (C.I. Pigment Red 179) prepared in accordance with Example 2a are mixed mechanically with 0.45 part of pigment dispersant of the formula IX prepared in accordance with Example 18.

This gives a pigment preparation which in the HS varnish gives transparent finishes of high color strength. The rheology is evaluated as 4 to 5 and the gloss measurement gives the value 73. The metallic finish is strongly colored and bright.

EXAMPLE 19

A stirred vessel is charged with 300 parts of 3,3'-iminobispropylamine and 30 parts of perylene-3,4,9,10-tetracarboxylic monoanhydride monomethylimide are introduced. The mixture is subsequently heated to 140° C. and stirred at 140° C. for 2 hours. After cooling to 25° C., 600 parts of water are added, the pigment dispersant is filtered off with suction and washed with water. The filtercake is introduced into 800 parts of 1% potassium hydroxide solution, which is then heated to 90° C. and stirred at 90° C. for 1 hour. The mixture is then filtered with suction at 90° C. and the solid product is washed with 1% strength potassium hydroxide solution until the runoff is colorless. Subsequently, the pigment dispersant is washed with water to neutrality and is dried at 80° C.

This gives 33.8 parts of pigment dispersant of the formula IX.

| Analysis: | calc.: 72% C |
|---|---|
|  | found: 72% C |

The $^1$H-NMR spectrum agrees with the structural formula indicated above, the signals lying at a shift δ of 8.7 ppm, 6.1 ppm, 5.7 ppm, 4.2 ppm, 3.5 ppm, 3.0 ppm, 2.8 ppm, 2.0 ppm and 1.8 ppm.

EXAMPLE 19a 10 parts of pigment (C.I. Pigment Red 179) prepared in accordance with Example 2a are mixed mechanically with 1.35 parts of pigment dispersant of the formula IX prepared in accordance with Example 19.

This gives a pigment preparation which in the HS varnish gives transparent finishes of high color strength. The rheology is evaluated as 4 to 5 and the gloss measurement gives the value 67. The metallic finish is strongly colored and bright.

EXAMPLE 20

10 parts of a commercial pigment (C.I. Pigment Red 179) prepared from 1,8-naphthalimide using an alkaline melt with subsequent methylation are mixed mechanically with 0.5 part of pigment dispersant of the formula IX prepared in accordance with Example 2.

The pigment preparation obtained is used to prepare a finish in the HS varnish, and a finish in the HS varnish is also prepared with the commercial pigment (C.I. Pigment Red 179) used for the preparation. Comparison of the finishes shows that the transparency is notably improved by the use of the pigment dispersant and the rheology is increased from 3 to 4 to 5. Without the use of the pigment dispersant the viscosity is so high that it cannot be measured with the viscospatula. Through the use of the pigment dispersant it is 1.6 s. The value of the gloss measurement is raised from 32 to 76.

EXAMPLE 21 (COMPARATIVE EXAMPLE)

The pigment dispersant of the formula XII is prepared in accordance with U.S. Pat. No. 4,762,569, Example 1.

| Analysis: | calc.: 9.1% N |
|---|---|
| | found: 8.8% N |

$^1$H-NMR spectrum (D$_2$SO$_4$): δ 8.7; 4.1; 2.87; 2.8; 1.9 and 0.9 ppm.

EXAMPLE 21a (COMPARATIVE EXAMPLE)

30 parts of pigment (C.I. Pigment Red 179) prepared in accordance with Example 2a are mixed mechanically with 1.35 parts of pigment dispersant of the formula XII prepared in accordance with Example 21.

This pigment preparation in the HS varnish gives a finish whose rheology in comparison to that of the pigment preparation of Example 7 (instead of 1.35 parts of pigment dispersant of the formula XII prepared in accordance with Example 21, 1.35 parts of pigment dispersant of the formula IX prepared in accordance with Example 2 were used for mechanical mixing) is markedly poorer. The solvent fastness is inadequate and is therefore markedly inferior to the solvent fastness of the pigment preparation of Example 7.

EXAMPLE 22

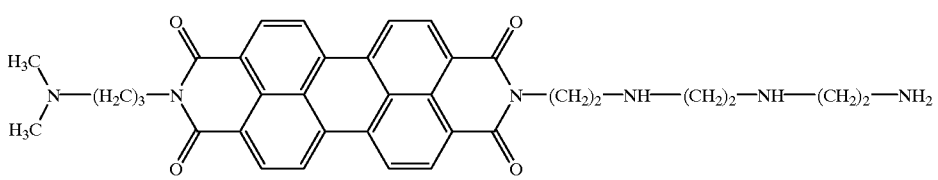

(XXI)

An autoclave is charged with 900 parts of water, 44.8 parts of perylene-3,4,9,10-tetracarboxylic monoanhydride mono(dimethylaminopropyl)imide are introduced, and 58.4 parts of triethylenetetramine are added. The mixture is subsequently heated under pressure to 150° C. and stirred at 150° C. for 5 hours. After cooling to 25° C., the pigment dispersant is filtered off with suction and washed to neutrality with water. This gives 392.9 parts of a 12.4% pigment dispersant presscake. A portion is dried at 80° C. for analysis and for mechanical mixtures.

| Analysis: | calc.: 69.5% C |
|---|---|
| | found: 69.3% C |

$^1$H-NMR spectrum (D$_2$SO$_4$): δ 8.7; 6.6; 6.9; 4.4; 4.1; 3.3; 2.9; 2.5 and 1.9 ppm.

EXAMPLE 22a 30 parts of pigment (C.I. Pigment Red 179) prepared in accordance with Example 2a are mixed mechanically with 1.35 parts of pigment dispersant of the formula XXI prepared in accordance with Example 22.

This gives a pigment preparation which in the HS varnish gives transparent finishes of high color strength. The rheology is evaluated as 4. The metallic finish is strongly colored and bright.

EXAMPLE 23

(XXII)

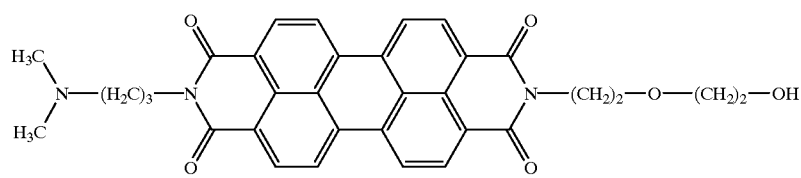

An autoclave is charged with 900 parts of water, 44.8 parts of perylene-3,4,9,10-tetracarboxylic monoanhydride mono(dimethylaminopropyl)imide are introduced, and 42 parts of 2-(2-aminoethoxy)ethanol are added. The mixture is subsequently heated under pressure to 150° C. and stirred at 150° C. for 5 hours. After cooling to 25° C., the pigment dispersant is filtered off with suction and washed to neutrality with water.

This gives 129.3 parts of a 37.3% pigment dispersant presscake. A portion is dried at 80° C. for analysis and for mechanical mixtures.

| Analysis: | calc.: 7.5% N |
|---|---|
| | found: 7.4% N |

$^1$H-NMR spectrum (D$_2$SO$_4$): δ 8.7; 5.2; 4.4; 4.2; 4.1; 2.9; 2.5 and 2.0 ppm.

EXAMPLE 23a 30 parts of pigment (C.I. Pigment Red 179) prepared in accordance with Example 2a are mixed mechanically with 1.35 parts of pigment dispersant of the formula XXII prepared in accordance with Example 23.

This gives a pigment preparation which in the HS varnish gives transparent finishes of high color strength. The rheology is evaluated as 4. The metallic finish is strongly colored and bright. The gloss measurement gives the value 74.

EXAMPLE 24

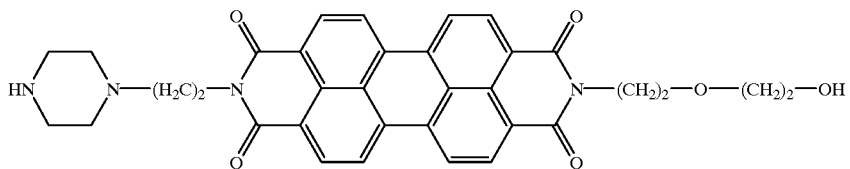

(XXIII)

An autoclave is charged with 900 parts of water, 47.9 parts of perylene-3,4,9,10-tetracarboxylic monoanhydride mono(2-(2-hydroxyethoxy)ethyl)imide are introduced, and 51.6 parts of N-(2-aminoethyl)piperazine are added. The mixture is subsequently heated under pressure to 150° C. and stirred at 150° C. for 5 hours. After cooling to 90° C., the pH is adjusted to 8–8.5 with acetic acid and the pigment dispersant is filtered off with suction and washed to neutrality with water.

This gives 215.4 parts of a 22.7% pigment dispersant presscake. A portion is dried at 80° C. for analysis and for mechanical mixtures.

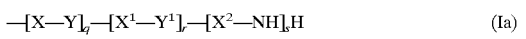

| Analysis: | calc.: 9.5% N |
| --- | --- |
| | found: 10.0% N |

$^1$H-NMR spectrum (D$_2$SO$_4$): δ 8.7; 6.6; 6.4; 5.2; 4.4; 4.2; 3.7; 3.5 and 3.2 ppm.

EXAMPLE 24a 30 parts of pigment (C.I. Pigment Red 179) prepared in accordance with Example 2a are mixed mechanically with 1.35 parts of pigment dispersant of the formula XXIII prepared in accordance with Example 24.

This gives a pigment preparation which in the HS varnish gives transparent finishes of high color strength. The rheology is evaluated as 4 to 5. The metallic finish is strongly colored and bright. The gloss measurement gives the value 64.

What is claimed is:

1. A perylene compound of formula (I)

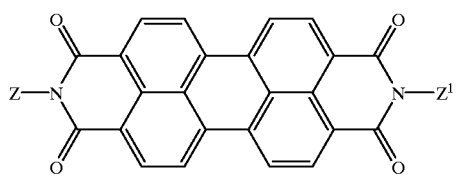

(I)

in which

Z$^1$ is a radical of formula (Ia)

—[X—Y]$_q$—[X$^1$—Y$^1$]$_r$—[X$^2$—NH]$_s$H     (Ia)

in which X, X$^1$ and X$^2$ are identical or different and are a branched or unbranched C$_2$–C$_6$-alkylene radical or a C$_5$–C$_7$-cycloalkylene radical which are optionally substituted by from 1 to 4 C$_1$–C$_4$-alkyl radicals, hydroxyl radicals, hydroxyalkyl radicals having 1 to 4 carbon atoms, or by from 1 to 2 C$_5$–C$_7$cycloalkyl radicals or are substituted by a combination thereof;

Y is an —NH—, —O— or —N(C$_1$–C$_6$-alkyl) group,

Y$^1$ is —NH— or —O—, q is a number from 1 to 6, r and s independently of one another are a number from 0 to 6, but are not simultaneously zero, and s is different from zero, if Y$^1$ is —O—; and Z is defined as Z$^1$, Z$^2$, or Z$^3$, where Z$^2$ is a radical of the formula (Ib)

—[X—O]$_{q1}$—[X$^1$—O]$_r$H     (Ib)

in which q1 is a number from 0 to 6, and Z$^3$ is hydrogen, hydroxyl, amino or unsubstituted C$_1$–C$_8$-alkyl or C$_1$–C$_8$-alkyl substituted by from 1 to 4 substituents from the group consisting of Cl, Br, CN, OH, C$_6$H$_5$, carbamoyl, C$_1$–C$_4$-acyl, C$_1$–C$_4$-alkoxy and NR$^2$R$^3$, or is perfluorinated or partly fluorinated, and where R$^2$ and R$^3$ independently of one another are a hydrogen atom, a substituted or unsubstituted or partly fluorinated or perfluorinated alkyl group of 1 to 20 carbon atoms, or a substituted or unsubstituted or partly fluorinated or perfluorinated alkenyl group of 2 to 20 carbon atoms, where the substituents are hydroxyl, phenyl, cyano, chloro, bromo, C$_2$–C$_4$-acyl or C$_1$–C$_4$-alkoxy, or R$^2$ and R$^3$, together with the adjacent nitrogen atom, form a saturated, unsaturated or aromatic heterocyclic ring which optionally contains a further nitrogen, oxygen or sulfur atom in the ring.

2. The perylene compound as claimed in claim 1, wherein X, X$^1$ and X$^2$ are a C$_2$–C$_4$-alkylene radical or cyclohexylene.

3. The perylene compound as claimed in claim 1, wherein Z$^1$ is

—(CH$_2$)$_3$—NH—(CH$_2$)$_3$—NH$_2$,

—(CH$_2$)$_2$—NH—(CH$_2$)$_2$—NH$_2$,

—(CH$_2$)$_3$—NH—(CH$_2$)$_2$—NH—(CH$_2$)$_3$—NH$_2$,

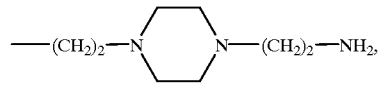

—(CH$_2$)$_3$—N(CH$_3$)—(CH$_2$)$_3$—NH$_2$,
—(CH$_2$)$_3$—O—(CH$_2$)$_2$—O—(CH$_2$)$_3$—NH$_2$,
—(CH$_2$)$_3$—O—(CH$_2$)$_3$—O—(CH$_2$)$_3$—NH$_2$,
—(CH$_2$)$_2$—NH—(CH$_2$)$_3$—NH$_2$,
—(CH$_2$)$_3$—NH—(CH$_2$)$_2$—NH$_2$,
—(CH$_2$)$_2$—NH—(CH$_2$)$_2$—NH—(CH$_2$)$_2$—NH$_2$,
—(CH$_2$—CH$_2$—NH)$_4$—H,
—(CH$_2$—CH$_2$—NH)$_5$—H or
—(CH$_2$)$_3$—O—(CH$_2$)$_4$—O—(CH$_2$)$_3$—NH$_2$.

4. The perylene compound as claimed in claim 1, wherein Z$^3$ is hydrogen, benzyl, C$_1$–C$_6$-alkyl or a C$_2$–C$_6$-alkyl which is substituted by from 1 to 2 substituents selected from the group consisting of hydroxyl, acetyl, methoxy and ethoxy.

5. The perylene compound as claimed in claim 1, wherein $Z^3$ is hydrogen, methyl, ethyl, propyl butyl, benzyl, hydroxyethyl, hydroxypropyl or methoxypropyl.

6. A perylene compound as claimed in claim 4, wherein $Z^3$ is a radical of the group —$(CH_2)_n$—$NR^2R^3$ in which n is a number from 1 to 6, and $R^2$ and $R^3$ independently of one another are a hydrogen atom, a $C_1$–$C_6$-alkyl group, a $C_1$–$C_6$-alkyl group which is substituted by from 1 to 2 substituents from the group consisting of hydroxyl, acetyl, methoxy, ethoxy, chloro and bromo, or $R^2$ and $R^3$, together with the adjacent nitrogen atom, form an imidazolyl, piperidinyl, morpholinyl, pipecolinyl, pyrrolyl, pyrrolidinyl, pyrazolyl or piperazinyl ring.

7. The perylene compound as claimed in claim 6, wherein n is the number 2 or 3, and $R^2$ and $R^3$ are each a methyl or ethyl group or $R^2$ and $R^3$, together with the nitrogen atom of the —$(CH_2)n$—$NR^2R^3$ group, form an imidazolyl, piperazinyl or morpholinyl radical.

8. The perylene compound as claimed in claim 1, wherein $Z^2$ has one of the definitions —$CH(CH_2OH)_2$ or —$(CH_2)_2$—O—$(CH_2)_2OH$.

9. The perylene compound as claimed in claim 1, wherein $Z^2$ is a radical of the formula (Ib) and $Z^3$ is hydrogen, hydroxyl, amino or unsubstituted $C_1$–$C_8$-alkyl or $C_1$–$C_8$-alkyl substituted by from 1 to 4 substituents from the group consisting of Cl, Br, CN, OH, $C_6H_5$, carbamoyl, $C_1$–$C_4$-acyl and $C_1$–$C_4$-alkoxy or is perfluorinated or partly fluorinated.

10. A process for preparing a perylene compound of formula (I)

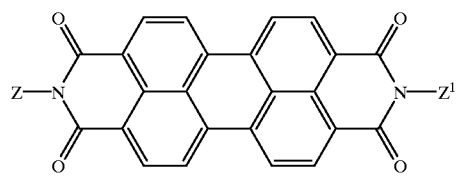

(I)

in which $Z^1$ is a radical of formula (Ia)

(Ia)

in which X, $X^1$ and $X^2$ are identical or different and are a branched or unbranched $C_2$–$C_6$-alkylene radical or a $C_5$–$C_7$-cycloalkylene radical which are optionally substituted by from 1 to 4 $C_1$–$C_4$-alkyl radicals, hydroxyl radicals, hydroxyalkyl radicals having 1 to 4 carbon atoms, or by from 1 to 2 $C_5$–$C_7$-cycloalkyl radicals or are substituted by a combination thereof;

Y is an —NH—, —O— or —N($C_1$–$C_6$-alkyl) group, $Y^1$ is —NH— or —O—, q is a number from 1 to 6, r and s independently of one another are a number from 0 to 6, but are not simultaneously zero, and s is different from zero, if $Y^1$ is —O—; and Z is defined as $Z^1$, $Z^2$, or $Z^3$, where $Z^2$ is a radical of the formula (Ib)

(Ib)

in which q1 is a number from 0 to 6, and $Z^3$ is hydrogen, hydroxyl, amino or unsubstituted $C_1$–$C_8$-alkyl or $C_1$–$C_8$-alkyl substituted by from 1 to 4 substituents from the group consisting of Cl, Br, CN, OH, $C_6H_5$, carbamoyl, $C_1$–$C_4$-acyl, $C_1$–$C_4$-alkoxy and $NR^2R^3$, or is perfluorinated or partly fluorinated, and where $R^2$ and $R^3$ independently of one another are a hydrogen atom, a substituted or unsubstituted or partly fluorinated or perfluorinated alkyl group of 1 to 20 carbon atoms, or a substituted or unsubstituted or partly fluorinated or perfluorinated alkenyl group of 2 to 20 carbon atoms, where the substituents are hydroxyl, phenyl, cyano, chloro, bromo, $C_2$–$C_4$-acyl or $C_1$–$C_4$-alkoxy, or $R^2$ and $R^3$, together with the adjacent nitrogen atom, form a saturated, unsaturated or aromatic heterocyclic ring which optionally contains a further nitrogen, oxygen or sulfur atom in the ring; the process comprising:

reacting a perylene-3,4,9,10-tetracarboxylic monoanhydride monoimide of the formula (IIa)

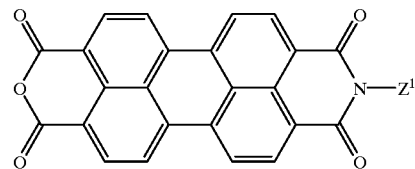

(IIa)

with one or more amines of the formula (IIIa) or (IIIb)

(IIIa)

(IIIb);

or by reacting a perylene-3,4,9,10-tetracarboxylic monoanhydride monoimide of the formula (IIb)

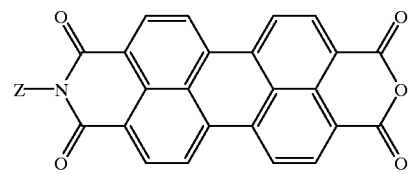

(IIb)

with one or more amines of the formula (IIIb);

or by reacting perylene-3,4,9,10-tetracarboxylic dianhydride of the formula (IIc)

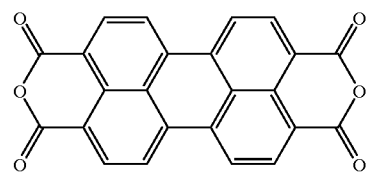

(IIc)

with one or more amines of the formula (IIIb).

11. A pigment preparation comprising:
a) at least one organic pigment selected from the group consisting of perylene pigment, perinone pigment, phthalocyanine pigment, dioxazine pigment, quinacridone pigment, azo pigment, anthraquinone pigment, aminoanthraquinone pigment, thioindigo pigment, diketopyrrolopyrrole pigment, flavanthrone pigment, indanthrone pigment, isoindoline pigment, isoindolinone pigment, anthrapyrimidine pigment, pyranthrone pigment, quinophthalone pigment, isovioanthrone pigment, triarylcarbonium pigment, carbon black pigment, anthanthrone pigment and a mixture thereof, and b) 0.5 to 40% by weight, based on the weight of the organic pigment, of at least one pigment dispersant of the formula (IV)

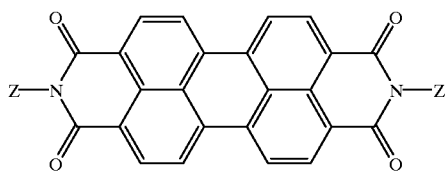

(IV)

in which the two radicals Z are identical or different and are defined as $Z^1$, $Z^2$, or $Z^3$, where $Z^1$ is a radical of formula (Ia)

(Ia)

in which X, $X^1$ and $X^2$ are identical or different and are a branched or unbranched $C_2$–$C_6$-alkylene radical or a $C_5$–$C_7$-cycloalkylene radical which are optionally substituted by from 1 to 4 $C_1$–$C_4$-alkyl radicals, hydroxyl radicals, hydroxyalkyl radicals having 1 to 4 carbon atoms, or by from 1 to 2 $C_5$–$C_7$-cycloalkyl radicals or are substituted by a combination thereof;

Y is an —NH—, —O— or —N($C_1$–$C_6$-alkyl) group,
$Y^1$ is —NH— or —O—,
q is a number from 1 to 6,
r and s independently of one another are a number from 0 to 6, but are not simultaneously zero, and s is different from zero, if $Y^1$ is —O—; and
$Z^2$ is a radical of the formula (Ib)

(Ib)

in which
q1 is a number from 0 to 6,
and $Z^3$ is hydrogen, hydroxyl, amino or unsubstituted $C_1$–$C_8$-alkyl or $C_1$–$C_8$-alkyl substituted by from 1 to 4 substituents from the group consisting of Cl, Br, CN, OH, $C_6H_5$, carbamoyl, $C_1$–$C_4$-acyl, $C_1$–$C_4$-alkoxy and $NR^2R^3$, or is perfluorinated or partly fluorinated, and where $R^2$ and $R^3$ independently of one another are a hydrogen atom, a substituted or unsubstituted or partly fluorinated or perfluorinated alkyl group of 1 to 20 carbon atoms, or a substituted or unsubstituted or partly fluorinated or perfluorinated alkenyl group of 2 to 20 carbon atoms, where the substituents can be hydroxyl, phenyl, cyano, chloro, bromo, $C_2$–$C_4$-acyl or $C_1$–$C_4$-alkoxy, or $R^2$ and $R^3$, together with the adjacent nitrogen atom, form a saturated, unsaturated or aromatic heterocyclic ring which optionally contains a further nitrogen, oxygen or sulfur atom in the ring;
with the proviso that the two radicals Z are not simultaneously $Z^3$.

12. The Pigment Preparation as claimed in claim 11 consisting essentially of
a) from 40 to 99.5% by weight of at least one pigment,
b) from 0.5 to 40% by weight of at least one pigment dispersant of the formula (IV),
c) from 0 to 20% by weight of surface-active agents, and
d) from 0 to 20% by weight of other customary additives, the proportions of the respective components being based on the overall weight of the preparation (100% by weight).

13. A method of coloring high molecular mass organic materials of natural or synthetic origin comprising adding 0.1 to 10% by weight, based on the weight of the high molecular mass organic material to be colored, of a pigment preparation as defined in claim 11 into said organic material which is in the form of plastic masses, melts, spinning solutions, varnishes, paints, printing inks, electrophotographic toners, powder coating materials or inkjet inks.

14. A prepared pigment formulation consisting essentially of a pigment preparation as set forth in claim 11, and a high molecular mass organic material which is in the form of plastic masses, melts, spinning solutions, varnishes, paints, printing inks, electrophotographic toners, powder coating materials or inkjet inks.

15. A pigment preparation comprising:
a) at least one organic pigment selected from the group consisting of perylene pigment, perinone pigment, phthalocyanine pigment, dioxazine pigment, quinacridone pigment, azo pigment, anthraquinone pigment, aminoanthraquinone pigment, thioindigo pigment, diketopyrrolopyrrole pigment, flavanthrone pigment, indanthrone pigment, isoindoline pigment, isoindolinone pigment, anthrapyrimidine pigment, pyranthrone pigment, quinophthalone pigment, isovioanthrone pigment, triarylcarbonium pigment, carbon black pigment, anthanthrone pigment and a mixture thereof,
b1) 0.5 to 40% by weight, based on the weight of the organic pigment, of a pigment dispersant of the formula (IX)

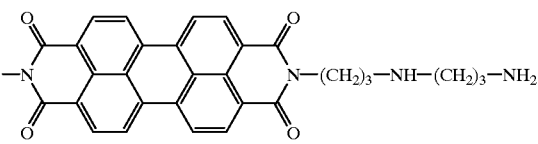

(IX)

and
b2) 0.5 to 40% by weight, based on the weight of the organic pigment, of a pigment dispersant of the formula (X)

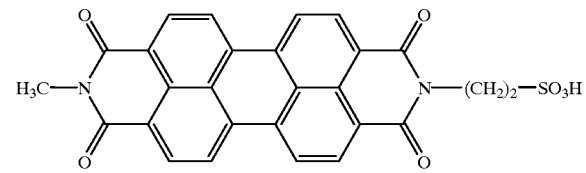

(X)

wherein the proportion of the pigment dispersant of the formula (IX) to the pigment dispersant of the formula (X) is between 1:10 and 10:1 parts by weight.

16. A process for preparing a pigment preparation, wherein the pigment preparation is comprised of:
a) at least one organic pigment selected from the group consisting of perylene pigment, perinone pigment, phthalocyanine pigment, dioxazine pigment, quinacridone pigment, azo pigment, anthraquinone pigment, aminoanthraquinone pigment, thioindigo pigment, diketopyrrolopyrrole pigment, flavanthrone pigment, indanthrone pigment, isoindoline pigment, isoindolinone pigment, anthrapyrimidine pigment, pyranthrone pigment, quinophthalone pigment, isovioanthrone pigment, triarylcarbonium pigment, carbon black pigment, anthanthrone pigment and a mixture thereof, and b) 0.5 to 40 % by weight, based on the weight of the organic pigment, of at least one pigment dispersant of the formula (IV)

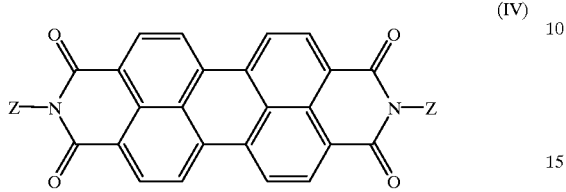

in which the two radicals Z are identical or different and are defined as $Z^1$, $Z^2$, or $Z^3$, where $Z^1$ is a radical of formula (Ia)

 (Ia)

in which X, $X^1$ and $X^2$ are identical or different and are a branched or unbranched $C_2$–$C_6$-alkylene radical or a $C_5$–$C_7$-cycloalkylene radical which are optionally substituted by from 1 to 4 $C_1$–$C_4$-alkyl radicals, hydroxyl radicals, hydroxyalkyl radicals having 1 to 4 carbon atoms, or by from 1 to 2 $C_5$–$C_7$-cycloalkyl radicals or are substituted by a combination thereof;

Y is an —NH—, —O— or —N($C_1$–$C_6$-alkyl) group,
$Y^1$ is —NH— or —O—,
q is a number from 1 to 6,
r and s independently of one another are a number from 0 to 6, but are not simultaneously zero, and s is different from zero, if $Y^1$ is —O—; and
$Z^2$ is a radical of the formula (Ib)

—[X—O]$_{q1}$—[$X^1$—O]$_q$H (Ib)

in which q1 is a number from 0 to 6, and $Z^3$ is hydrogen, hydroxyl, amino or unsubstituted $C_1$–$C_8$-alkyl or $C_1$–$C_8$-alkyl substituted by from 1 to 4 substituents from the group consisting of Cl, Br, CN, OH, C6H$_5$, carbamoyl, $C_1$–$C_4$-acyl, $C_1$–$C_4$-alkoxy and $NR^2R^3$, or is perfluorinated or partly fluorinated, and where $R^2$ and $R^3$ independently of one another are a hydrogen atom, a substituted or unsubstituted or partly fluorinated or perfluorinated alkyl group of 1 to 20 carbon atoms, or a substituted or unsubstituted or partly fluorinated or perfluorinated alkenyl group of 2 to 20 carbon atoms, where the substituents can be hydroxyl, phenyl, cyano, chloro, bromo, $C_2$–$C_4$-acyl or $C_1$–$C_4$-alkoxy, or $R^2$ and $R^3$, together with the adjacent nitrogen atom, form a saturated, unsaturated or aromatic heterocyclic ring which optionally contains a further nitrogen, oxygen or sulfur atom in the ring; with the proviso that the two radicals Z are not simultaneously $Z^3$; said process comprising:

adding the pigment dispersant of the formula (IV) prior to, during or after synthesis of the pigment; or adding the pigment dispersant of the formula (IV) prior to, during or after fine division of the pigment; or adding the pigment dispersant of the formula (IV) prior to, during or after solvent treatment of the pigment.

17. The process as claimed in claim 16, wherein the pigment dispersant, the organic pigment or both of them are combined in the form of a water-moist presscake or are mixed with one another as dry granules or powders.

* * * * *